US012594199B2

(12) United States Patent
Ehrnsperger et al.

(10) Patent No.: US 12,594,199 B2
(45) Date of Patent: Apr. 7, 2026

(54) ABSORBENT CORE WITH NONWOVEN WEB(S) COMPRISING SUPERABSORBENT FIBERS

(71) Applicant: The Procter & Gamble Company, Cincinnati, OH (US)

(72) Inventors: Bruno Johannes Ehrnsperger, Bad Soden (DE); Juliane Kamphus, Schwalbach (DE); Simone Seeboth, Schwalbach (DE); Saskia Kraemer, Hessen (DE)

(73) Assignee: The Procter & Gamble Company, Cincinnati, OH (US)

( * ) Notice: Subject to any disclaimer, the term of this patent is extended or adjusted under 35 U.S.C. 154(b) by 643 days.

(21) Appl. No.: 17/725,744

(22) Filed: Apr. 21, 2022

(65) Prior Publication Data

US 2022/0354713 A1 Nov. 10, 2022

(30) Foreign Application Priority Data

May 10, 2021 (EP) .................................... 21173030

(51) Int. Cl.
*A61F 13/15* (2006.01)
*A61F 13/536* (2006.01)
(Continued)

(52) U.S. Cl.
CPC .... *A61F 13/5376* (2013.01); *A61F 13/15723* (2013.01); *A61F 13/536* (2013.01);
(Continued)

(58) Field of Classification Search
CPC ............ A61F 13/5376; A61F 13/53747; A61F 13/536; A61F 13/15723;
(Continued)

(56) References Cited

U.S. PATENT DOCUMENTS

| | | | |
|---|---|---|---|
| 6,635,799 B1 | 10/2003 | Osborn, III et al. | |
| 2002/0143308 A1* | 10/2002 | Reeves .................. | C08G 65/30 |
| | | | 604/377 |

(Continued)

FOREIGN PATENT DOCUMENTS

| | | |
|---|---|---|
| EP | 0339461 A1 | 11/1989 |
| EP | 0887056 A1 | 12/1998 |

(Continued)

OTHER PUBLICATIONS

Extended EP Search Report and Search Opinion for 21173030.4 dated Oct. 21, 2021, 11 pages.
(Continued)

*Primary Examiner* — Jacqueline F Stephens
(74) *Attorney, Agent, or Firm* — Daniel S. Albrecht

(57) ABSTRACT

An absorbent core including one or more nonwoven webs with superabsorbent fibers. The superabsorbent fibers may include one or more surfactants. The one or more nonwoven webs have an amount of extractables of less than 20 weight-%, and/or an amount of titratable soluble of less than 20%. The nonwoven webs have a capacity of at least 7 g/g. The absorbent core may be used in an absorbent article.

19 Claims, 13 Drawing Sheets

(51) Int. Cl.
    *A61F 13/537*        (2006.01)
    *A61F 13/53*         (2006.01)

(52) U.S. Cl.
    CPC ................... *A61F 13/53747* (2013.01); *A61F 2013/15934* (2013.01); *A61F 2013/53062* (2013.01); *A61F 2013/5307* (2013.01); *A61F 2013/530715* (2013.01); *A61F 2013/530751* (2013.01)

(58) Field of Classification Search
    CPC ........ A61F 2013/530751; A61F 2013/530715; A61F 2013/5307; A61F 2013/53062; A61F 2013/15934
    See application file for complete search history.

(56)           References Cited

U.S. PATENT DOCUMENTS

| | | | |
|---|---|---|---|
| 2002/0173762 | A1 | 11/2002 | Ishikawa |
| 2003/0181884 | A1 | 9/2003 | Carstens et al. |
| 2009/0076473 | A1 | 3/2009 | Kasai et al. |
| 2009/0099541 | A1 | 4/2009 | Qin et al. |
| 2010/0068520 | A1* | 3/2010 | Stueven ............... C08F 220/06 526/317.1 |

| | | | |
|---|---|---|---|
| 2012/0316523 | A1 | 12/2012 | Hippe |
| 2015/0174280 | A1 | 6/2015 | Stelzig et al. |
| 2015/0292117 | A1* | 10/2015 | Daniel ...................... D01F 6/02 428/401 |
| 2017/0095379 | A1 | 4/2017 | Cipriani |
| 2018/0193517 | A1 | 7/2018 | Feldkamp et al. |
| 2018/0305519 | A1 | 10/2018 | Kamphus |
| 2018/0305523 | A1* | 10/2018 | Kamphus ................. C08J 3/203 |
| 2020/0315861 | A1* | 10/2020 | Viens ................... D04H 1/4258 |
| 2022/0362072 | A1 | 11/2022 | Jackels |

FOREIGN PATENT DOCUMENTS

| | | |
|---|---|---|
| EP | 1265649 B1 | 2/2005 |
| WO | 03052190 A1 | 6/2003 |
| WO | 2015002934 A2 | 1/2015 |

OTHER PUBLICATIONS

All Office Actions; U.S. Appl. No. 17/725,737, filed on Apr. 21, 2022.

PCT Search Report and Written Opinion for PCT/US2022/028253 dated Jul. 29, 2022, 16 pages.

\* cited by examiner

ABSORBENT CORE WITH NONWOVEN WEB(S) COMPRISING SUPERABSORBENT FIBERS

FIELD OF THE INVENTION

The invention relates to an absorbent core and an absorbent article comprising the absorbent core as well as to a method of making the absorbent core. The absorbent core comprises one or more nonwoven webs which comprise superabsorbent fibers with surfactant. The superabsorbent fibers have relatively low amount of extractables.

BACKGROUND OF THE INVENTION

The use of water-swellable, generally water-insoluble absorbent materials, commonly known as superabsorbers, in absorbent articles is well known. Such absorbent materials are employed in absorbent cores of absorbent articles such as diapers, training pants, adult incontinence products, and feminine care articles in order to increase the absorbent capacity of such articles while reducing their overall bulk and/or weight. To date, such absorbent materials are generally present as superabsorbent particles, often in combination with a fibrous matrix, such as a matrix of wood pulp fluff. However, absorbent cores without a fibrous matrix are also known.

Absorbent cores formed of superabsorbent particles in the absence of pulp fluff are sometimes difficult to use because the superabsorbent particles do not remain stationary during manufacturing process of the absorbent core and may also shift position during use of the absorbent article upon liquid absorption and swelling. Moreover, while superabsorbent particles enable thin absorbent cores, they cannot readily be converted into a coherent, self-sustaining layer, such as a nonwoven web. Instead, adhesives are typically used to immobilize the superabsorbent polymer particles on a carrier layer (such as a nonwoven web). However, layers of superabsorbent polymer particles immobilized by adhesives have a tendency to be stiff and grainy, especially while they are still dry. To counterbalance the stiffness and graininess, additional layers may be provided above and/or below the absorbent core to provide a softer feel to the article. Additional layers may also be needed to enable an efficient absorbent system that is able to acquire, temporarily hold and distribute urine before the liquid is finally stored and "locked" in the superabsorbent polymer particles. All this has led to a general increase in cost and complexity of absorbent articles.

Superabsorbent fibers have the advantage that they can be readily turned into a nonwoven web. This can reduce or eliminate the need for dry and wet immobilization of the superabsorbent polymer particles with adhesives as well as eliminate the need for wrapping and encapsulating the immobilized superabsorbent particles. Thereby, the need for "cushioning" layers above and/or below the absorbent core to increase softness can be eliminated.

However, the inventors have found that the acquisition rate of nonwoven webs formed of commercially available superabsorbent fibers is too low, so the need for absorbent cores are not met. Low acquisition rates typically lead to liquid run off from the absorbent article and, thus, leakage of urine out of the absorbent article, as the urine cannot be absorbed fast enough. This is especially applicable if the absorbent article is not provided with additional components to temporarily hold the liquid (often referred to as acquisition layers). This finding was surprising because the specific surface area of superabsorbent fibers is substantially higher than the specific surface area of superabsorbent particles, and hence, superabsorbent fibers were believed to have the potential to absorb urine at urination rates, eliminating the need for an acquisition system.

Hence, there is a need to address the above-mentioned drawbacks to provide an absorbent core comprising one or more nonwoven webs with superabsorbent fibers which exhibit fast liquid acquisition.

SUMMARY OF THE INVENTION

The present invention relates to an absorbent core comprising one or more nonwoven webs. The nonwoven webs comprise at least 80 weight-%, or at least 85 weight-%, or at least 90 weight-%, or at least 95 weight-%, or at least 98 weight-% of superabsorbent fibers based on the total weight of the respective nonwoven web (hereinafter referred to as "nonwoven webs with superabsorbent fibers"). The superabsorbent fibers comprise one or more surfactant(s). Each of the nonwoven webs has a capacity of at least 7 g/g, or at least 8 g/g, or at least 10 g/g, or at least 12 g/g, or at least 15 g/g, or at least 18 g/g, or at least 20 g/g as measured according to the Centrifuge Retention Capacity test set out herein.

Each of the nonwoven webs with superabsorbent fibers may have a basis weight of at least 50 g/m$^2$, or at least 100 g/m$^2$, or at least 150 g/m$^2$, or at least 200 g/m$^2$. Each nonwoven web may have a basis weight of not more than 1000 g/m$^2$, or not more than 800 g/m$^2$, or not more than 600 g/m$^2$, or not more than 500 g/m$^2$.

The absorbent core may have a total basis weight of from 100 g/m$^2$ to 1000 g/m$^2$, or from 200 g/m$^2$ to 800 g/m$^2$, or from 400 g/m$^2$ to 800 g/m$^2$, or from 500 g/m$^2$ to 800 g/m$^2$.

The absorbent core as a whole comprises at least 60 weight-%, or at least 70 weight-%, or at least 75 weight-%, or at least 80 weight-%, or at least 90 weight-%, or at least 95 weight-%, or at least 98 weight-% of the superabsorbent fibers based on the total weight of the absorbent core.

The absorbent core as a whole may have a capacity of at least 7 g/g, or at least 8 g/g, or at least 10 g/g, or at least 12 g/g, or at least 15 g/g, or at least 18 g/g, or at least 20 g/g as measured according to the Centrifuge Retention Capacity test set out herein.

The superabsorbent fibers comprised by the absorbent core may have a capacity of at least 7 g/g, or at least 8 g/g, or at least 10 g/g, or at least 12 g/g, or at least 15 g/g, or at least 18 g/g, or at least 20 g/g as measured according to the Centrifuge Retention Capacity test set out herein.

The nonwoven web(s) with superabsorbent fibers may have an amount of extractables of less than 20 weight-%, or less than 15 weight-%, or less than 12 weight-%, or less than 10 weight-% based on the total weight of the nonwoven web(s) with superabsorbent fibers according to the Extractables Test Method set out herein. Alternatively or in addition, the nonwoven web(s) with superabsorbent fibers may have an amount of titratable soluble of less than 20%, or less than 18%, or less than 15%, or less than 12%, or less than 10%, or less than 8%, or less than 6%, or less than 4% according to the Titratable Soluble Test Method set out herein.

If the amount of extractables of the nonwoven web(s) with superabsorbent fibers is higher than 20 weight-%, and/or the amount of titratable soluble nonwoven web(s) with superabsorbent fibers is higher than 20%, it has been found that the high amount of extractables and titratable soluble, which escape from the nonwoven web(s) with superabsorbent fibers upon wetting, considerably block the void space in the interstices in the one or more nonwoven webs. At such elevated levels of titratable soluble, liquid cannot spread and be sufficiently distributed within the one or more nonwoven webs to enable fast liquid acquisition. Also, extractables which escaped from the nonwoven web(s) with superabsorbent fibers upon wetting increase the viscosity of the liquid that enters the absorbent core, thus slowing down acquisition times. The amount of extractables of the nonwoven web(s) with superabsorbent fibers can be reduced e.g. by increasing the crosslinking level in the superabsorbent fibers, and/or by heating the nonwoven web with superabsorbent fibers.

If the amount of titratable soluble of the nonwoven web(s) with superabsorbent fibers is higher than 20%, it has been found that the high amount of titratable soluble that escape from the nonwoven web(s) with superabsorbent fibers upon wetting considerably reduce the osmotic capacity of the nonwoven web(s) with superabsorbent fibers by decreasing the amount of charged components inside the superabsorbent fibers and by increasing the amount of charged components outside the superabsorbent fibers. At such excessive levels of titratable soluble, the nonwoven web(s) with superabsorbent fibers cannot absorb sufficiently the liquid in the nonwoven web(s) with superabsorbent fibers to enable fast liquid acquisition. Also, titratable soluble which escaped from the nonwoven web(s) with superabsorbent fibers upon wetting increase the viscosity of the liquid that enters the absorbent core, thus slowing down acquisition times. The amount of titratable soluble of the nonwoven web(s) with superabsorbent fibers can be reduced e.g. by increasing the crosslinking level of the superabsorbent fibers, and/or by heating the nonwoven web with superabsorbent fibers.

The amount of extractable reflects all substances (e.g. monomers, oligomers, soluble polymers etc.) which can "escape" from the superabsorbent fibers or the nonwoven web(s) with superabsorbent fibers, respectively, upon wetting, thus also including neutral extractables, which negatively impacts (i.e. increases) viscosity of the liquid (typically urine) absorbed by the absorbent core. An increase in viscosity generally leads to a reduction of liquid flow in a porous structures (such as a nonwoven web) and thereby to a reduction in the speed at which the liquid is absorbed by the absorbent core comprising nonwoven webs with superabsorbent fibers. The amount of titratable soluble is focused on the substances (e.g. monomers, oligomers, soluble polymers etc.) which are dissolved via extraction from the superabsorbent fibers or the nonwoven web(s) with superabsorbent fibers, respectively and which can be titrated via base-acid titration. Typically, these substances are, at least at specific pH-ranges, negatively or positively charged (e.g. bear acidic or basic groups, are protonated or deprotonated) that "escape" from the superabsorbent fibers or the nonwoven web(s) with superabsorbent fibers, respectively. These substances can, beyond negative impact on liquid viscosity, impact the osmotic balance between the inside of the superabsorbent fiber and the surrounding environment, leading to a reduction of the osmotic capacity of the superabsorbent fibers. The more charged substances are outside the superabsorbent fibers, the more the osmotic capacity is reduced and the slower is the acquisition speed of the absorbent core comprising nonwoven webs with superabsorbent fibers.

The superabsorbent fibers comprised by the nonwoven web(s) of the absorbent core may have an amount of extractables of less than 20 weight-%, or less than 15 weight-% or less than 12 weight-%, or less than 10 weight-% based on the total weight of the superabsorbent fibers according to the Extractables Test Method set out herein. Alternatively or in addition, the superabsorbent fibers may have an amount of titratable soluble of less than 20%, or less than 18%, or less than 15%, or less than 12%, or less than 10%, or less than 8%, or less than 6%, or less than 4% according to the Titratable Soluble Test Method set out herein.

If the amount of extractables of the superabsorbent fibers is higher than 20 weight-%, it has been found that the extractables, which escape from the superabsorbent fibers upon wetting, considerably block the void space in the interstices between the superabsorbent fibers. Consequently, liquid cannot spread and be sufficiently distributed between the superabsorbent fibers to enable fast liquid acquisition. Also, extractables which escaped from the superabsorbent fibers upon wetting increase the viscosity of the liquid that enters the absorbent core, thus slowing down acquisition times. The amount of extractables can be reduced e.g. by increasing the crosslinking level of the superabsorbent fibers, and/or by heating the superabsorbent fibers.

If the amount of titratable soluble of the superabsorbent fibers is higher than 20%, a high amount of titratable soluble escape from the superabsorbent fibers upon wetting and considerably reduce the osmotic capacity of the superabsorbent fibers by decreasing the amount of charged components inside the superabsorbent fibers and by increasing the amount of charged components outside the superabsorbent fibers. Consequently, the superabsorbent fibers cannot absorb sufficiently the liquid distributed between the superabsorbent fibers to enable fast liquid acquisition. Also, titratable soluble which escaped from the superabsorbent fibers upon wetting increase the viscosity of the liquid that enters the absorbent core, thus slowing down acquisition times. The amount of titratable soluble can be reduced e.g. by increasing the crosslinking level of the superabsorbent fibers, and/or by heating the superabsorbent fibers.

Absorbent articles comprising such absorbent core are also comprised by the invention, as well as a method of making the absorbent core.

The absorbent core may form the only component of the absorbent system of the absorbent article. Thus, the absorbent article may not comprise any additional components above and/or below the absorbent core for liquid handling or softness.

Alternatively, the absorbent article may have a topsheet above (towards the skin of the wearer) and/or a backsheet below (towards the garment of the wearer) the absorbent core.

In use conditions of the absorbent core, comprised by an absorbent article, is often subjected to pressure exerted by the wearer, e.g. while sitting or lying. Therefore, it is desirable that the absorbent core is able to acquire fluid at meaningful rates under pressure typical for in use conditions. Fluid should be able to move inside the voids created by the superabsorbent fibers of the absorbent core also under a confined pressure. Moreover, movement of fluid within these voids should be feasible even if the absorbent core is already partially loaded with fluid, e.g. from previous insults of urine. Hence, it is desirable that the dry fiber structure has relatively high porosity, such as more than 90%, or more than 93%, or even more than 95%. Porosity can be calculated from basis weight, caliper, and specific fiber density, as is set out in more detail below.

In the present invention, the nonwoven webs comprising at least 80 weight-% of superabsorbent fibers based on the total weight of the nonwoven web, may each have a porosity of at least 90%, or at least 93%, or at least 95%, or at least 97%, as measured according to the porosity test method set out herein.

Moreover, it is desirable that the dry superabsorbent fibers of the one or more nonwoven webs are mechanically entangled, such as by needle-punching. Fiber entanglement and suitable initial porosity can provide sufficient interconnected void space within the absorbent core, even under pressure.

Also, the dry superabsorbent fibers are desirably hydrophilic. If the fibers are hydrophobic, then liquid may likely not move (spread) within the absorbent core even though the absorbent core may have sufficient void space. Fibers can, for example, be made sufficiently hydrophilic by application of one or more surfactants.

The present invention also relates to absorbent articles comprising the absorbent cores described above and below. The absorbent article may comprise a topsheet and a backsheet, and the absorbent core of the present invention may be provided between the topsheet and the backsheet. The absorbent article may further comprise an acquisition system of one or more layers (preferably one or two) which are provided between the absorbent core and the topsheet.

Further, the present invention relates to a method of making the absorbent cores described above and below.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION OF THE INVENTION

Definitions

Figure 1:
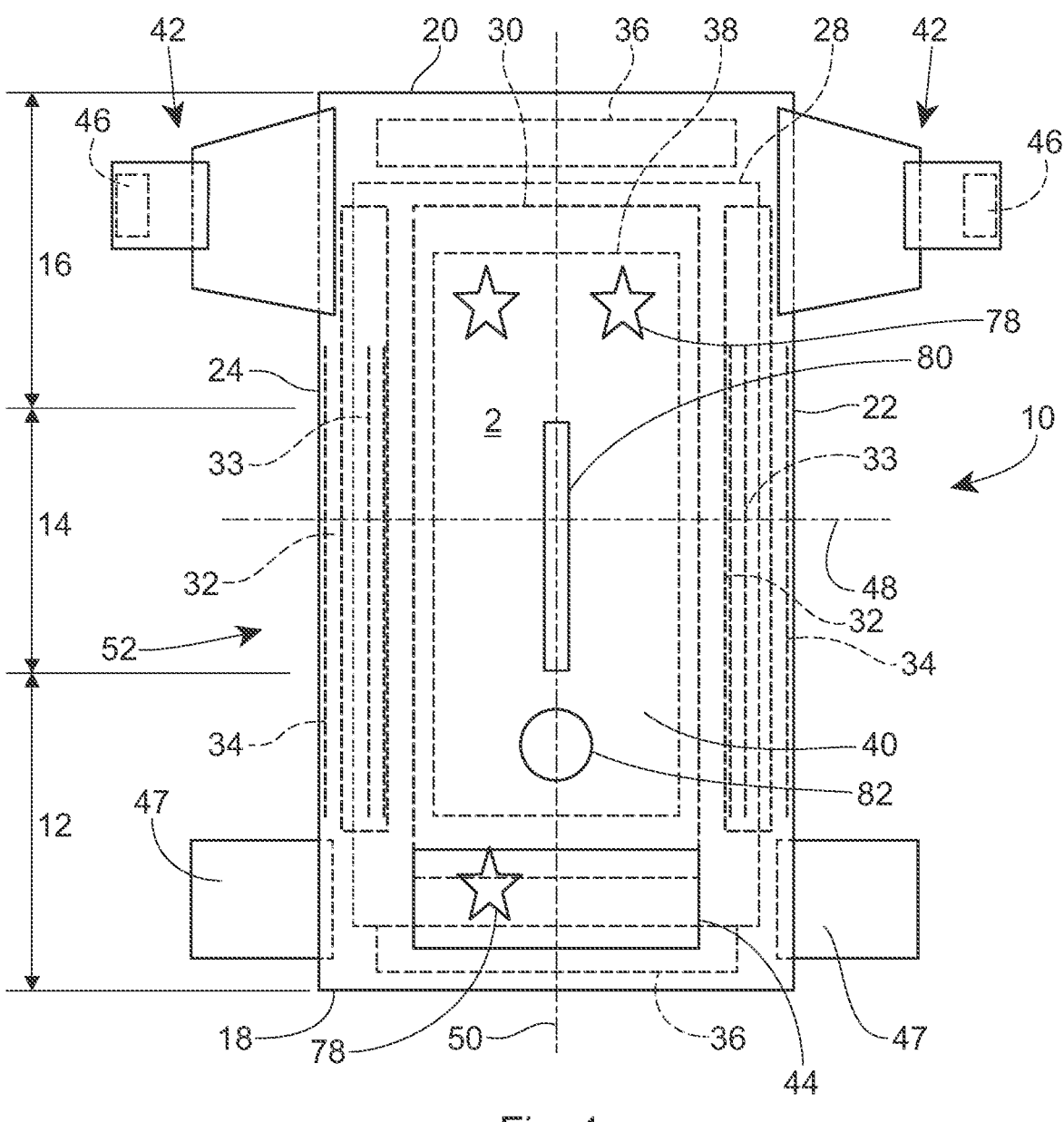
FIG. 1 is a plan view of an example absorbent article in the form of a taped diaper, garment-facing surface facing the viewer, in a flat laid-out state.

"Absorbent article" refers to devices that absorb and contain body exudates, particularly urine and other water-containing liquids, and, more specifically, refers to devices that are placed against or in proximity to the body of the wearer to absorb and contain the various exudates discharged from the body. Absorbent articles may include diapers (diapers for babies and infants and diapers to address adult incontinence), pants (pants for babies and infants and pants to address adult incontinence), disposable absorbent inserts for diapers and pants having a re-usable outer cover), feminine care absorbent articles such as sanitary napkins or pantiliners, breast pads, care mats, bibs, wipes, and the like. As used herein, the term "exudates" includes, but is not limited to, urine, blood, vaginal discharges, breast milk, sweat and fecal matter. Preferred absorbent articles of the present invention are disposable absorbent articles, more preferably disposable diapers, disposable pants and disposable absorbent inserts.

"Absorbent core" is used herein to refer to a structure intended to be disposed between a topsheet and backsheet of an absorbent article for absorbing and containing liquid received by the absorbent article.

"Airfelt" is used herein to refer to comminuted wood pulp, which is a form of cellulosic fiber.

"Disposable" is used in its ordinary sense to mean an article that is disposed or discarded after a limited number of usage events over varying lengths of time, for example, less than 10 events, less than 5 events, or less than 2 events. If the disposable absorbent article is a diaper, a pant, absorbent insert, sanitary napkin, sanitary pad or wet wipe for personal hygiene use, the disposable absorbent article is most often intended to be disposed after single use.

"Diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be pre-formed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

"Superabsorbent polymer material" ("SAP material") is used herein to refer to crosslinked polymeric materials that can absorb at least 7 times their weight of an aqueous 0.9 weight-% saline solution as measured using the Centrifuge Retention Capacity test set out below. Superabsorbent polymer material of the present invention contains polymers that comprise as monomer groups acrylic acid and/or acrylate and/or methacrylic acid and/or methacrylate.

As used herein, the term "SAF" refers to superabsorbent fibers. The SAF of the present invention are capable of absorbing a 0.9 weight % saline solution at 25° C. at least 7 times their dry weight, preferably at least 10 times their dry weight as measured according to the Centrifuge Retention Capacity (CRC) test as described herein. The typical absorption mechanism is osmotic pressure. SAF that absorb water or aqueous solutions become softer and gel-like.

"Superabsorbent fiber" ("SAF") is used herein to refer to superabsorbent polymer material that is in a fibrous form. The superabsorbent fibers have a length and a cross-section. The length is the largest dimension of the fiber when the fiber is or would be laid flat and straight on a surface, such that curves or crimps in the fiber disappear and the fiber becomes an approximately rod-like form. The cross-section is orthogonal to the length. For purposes herein, a fiber is a material that has a largest dimension and smallest dimension, wherein the ratio of largest dimension to smallest dimension is at least 10:1, preferably at least 15:1, even more preferably at least 20:1, i.e. the largest dimension of the superabsorbent fiber (also called the length) is at least 10 times, or at least 15 times, or at least 20 times the smallest dimension of the fiber (also called width). If a superabsorbent fiber has a cross-section that varies along the length of the fiber, the largest dimension of the cross-section (determined along the length of the fiber) is taken as the width of the fiber when calculating the ratio of largest dimension to smallest dimension.

"Superabsorbent polymer particles" ("SAP particles") is used herein to refer to superabsorbent polymer material that is in particulate form so as to be flowable in the dry state. Superabsorbent polymer particles are distinguished from the superabsorbent fibers of the present invention in that their ratio of largest to smallest dimension is not more than 10 to 1. Superabsorbent polymer particles may for example be in the form of granules, spheres, flakes or agglomerates.

As used herein, the term "nonwoven web" refers to a material which is a manufactured web/layer of directionally or randomly oriented fibers or filaments. The fibers may be of natural or man-made origin. Natural fibers may be selected from the group consisting of wheat straw fibers, rice straw fibers, flax fibers, bamboo fibers, cotton fibers, jute fibers, hemp fibers, sisal fibers, bagasse fibers, Hesper aloe fibers, *miscanthus*, marine or fresh water algae/seaweeds, silk fibers, wool fibers, and combinations thereof. Another group of fibers may also be regenerated cellulose fibers, such as viscose, Lyocell (Tencel®), rayon, modal, cellulose acetate fibers, acrylic fibers, cuprammonium rayon, regenerated protein fibers etc. Preferably, the natural fibers or modified natural fibers are selected from the group consisting of cellulose fibers (also referred to as pulp or airfelt) or modified cellulose fibers, such as intra-fiber crosslinked cellulose fibers, cotton fibers, bamboo fibers, viscose fibers or mixtures thereof. More preferably, the natural fibers or modified natural fibers are cellulose fibers or modified cellulose fibers. Synthetic fibers may be selected from the group consisting of polyolefins (such as polyethylene, polypropylene or combinations and mixtures thereof), polyethylene terephthalate (PET), co-PET, polylactic acid (PLA), polybutylene succinate (PBS), polyhydroxy alkanoid (PHA), nylon (or polyamide), or mixtures or combinations thereof.

The fibers in a nonwoven web are consolidated by friction, and/or entanglement, and/or cohesion, and/or adhesion, and/or by heat bonding, pressure bonding, or heat and pressure bonding, and/or ultrasonic bond, excluding paper and products which are woven, knitted, tufted, stitch-bonded. The fibers may be staple fibers (e.g. in carded nonwoven webs) or continuous fibers (e.g. in spunbonded or meltblown nonwoven webs).

The nonwoven webs comprised by the absorbent core of the present invention may comprise or may consist of superabsorbent fibers.

Nonwoven webs can be formed by many processes such as meltblowing, spunlaying, solvent spinning, electrospinning, and carding, and the fibers can be consolidated, e.g. by hydroentanglement (in spunlace nonwoven webs), air-through bonding (using hot air that is blown through the fiber layer in the thickness direction), infrared heat, needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers or particles (which are subsequently molten) or may be provided in liquid, such as a styrene butadiene binder. A liquid binder is provided to the fibers (e.g. by spraying, printing or foam application) and is subsequently cured to solidify.

The basis weight of nonwoven webs is usually expressed in grams per square meter (g/m²).

The nonwoven web, especially nonwoven webs consisting of or comprising superabsorbent fibers, may be carded webs formed by needle-punching. In needle punching, the fibers cohesion and the interlacing of the fibers with one another is obtained by means of needles passing through a moving fibrous layer and causing the fibers to intermingle with one another One or more, or all of the nonwoven webs of the absorbent core of the present invention may also be formed of two or more precursor webs, which are combined with each other by a needle punching process.

Alternatively, one or more, or all of the nonwoven webs of the absorbent core of the present invention may be formed by spunlacing. In a spunlace nonwoven web the fibers have been carded as precursor web and then subjected to hydroentanglement to intermingle and intertwine the fibers with each other. Cohesion and the interlacing of the fibers with one another may be obtained by means of a plurality of jets of water under pressure passing through a moving fleece or cloth and, like needles, causing the fibers to intermingle with one another (hereinafter also referred to as "hydraulic interlacing"). Thus, consolidation of a spunlace nonwoven web is essentially a result of hydraulic interlacing. "Spunlace nonwoven web", as used herein, also relates to a nonwoven web formed of two or more precursor webs, which are combined with each other by hydraulic interlacing.

The two or more webs, prior to being combined into one nonwoven by needle-punching or hydraulic interlacing, may have undergone bonding processes, such as heat and/or pressure bonding by using e.g. a patterned calendar roll and an anvil roll to impart a bonding pattern. However, the two or more webs are combined with each other solely by needle-punching or hydraulic interlacing.

Alternatively, the carded nonwoven web made by needle-punching or spunlacing is a single nonwoven web, i.e. it is not formed of two or more precursor webs. Still in another alternative, one or more, or all of the nonwoven webs of the absorbent core of the present invention may be formed of one precursor web onto which staple fibers are laid down.

The staple fibers may be superabsorbent fibers or may comprise superabsorbent fibers. The staple fibers may not have been consolidated into a self-sustaining precursor web but the fibers are loosely laid onto the precursor web. The relatively loose staple fibers are then integrated and intertwined with each other and with the fibers of the underlying precursor web by (only) needle-punching or (only) hydraulic interlacing. Spunlace and/or needle punched nonwoven layers/webs can be made of staple fibers or continuous fibers (continuous fibers are also often referred to as filaments).

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The melting and re-solidification of the polymer provide the bonding between different fibers.

"Comprise," "comprising," and "comprises" are open ended terms, each specifies the presence of the feature that follows, e.g. a component, but does not preclude the presence of other features, e.g. elements, steps, components known in the art or disclosed herein. These terms based on the verb "comprise" encompasses the narrower terms "consisting essentially of" which excludes any element, step or ingredient not mentioned which materially affect the way the feature performs its function, and the term "consisting of" which excludes any element, step, or ingredient not specified.

Superabsorbent Fibers

As said above, superabsorbent fibers were believed to have the potential for faster fluid acquisition than superabsorbent polymer particles due to their larger surface area per volume. However, absorbent cores comprising superabsorbent fibers, have been found to be actually worse in fluid acquisition properties than commercially available superabsorbent polymer particles. When being subjected to the fluid acquisition test set out herein below, the nonwoven webs with superabsorbent fibers of the Examples below have shown very low acquisition times, reflecting very good acquisition performance. The inventors have found that upon treating the nonwoven webs with superabsorbent fibers with a surfactant, the acquisition times have significantly improved.

Moreover, the nonwoven web with superabsorbent fibers with higher capacity were found to exhibit a considerable loss in integrity upon absorption and swelling. The web turned "slimy" and it has been determined that a considerable amount of liquid was not properly absorbed into the fibers but remained in the interstices between the fibers. As a consequence, the nonwoven webs have a tendency for high rewet, i.e. liquid is moving out of the absorbent core upon pressure, so in in-use conditions in an absorbent article, liquid can move back onto the wearer-facing surface of the article, e.g. when the wearer sits or otherwise applies pressure on the article. The "slimy" consistency also results in poor integrity of the wet absorbent core.

Upon further investigation to determine the cause for these observations, the inventors have found that nonwoven webs with superabsorbent fibers exhibiting the drawbacks described in the previous paragraph have a relatively high amount of extractables and/or titratable soluble.

Extractables and/or titratable soluble, often unreacted monomers, oligomers and non-crosslinked polymers, tend to leach out of the superabsorbent fibers once the fibers are swollen, thus adversely affecting superabsorbent properties both by loss of superabsorbent mass, and by the osmotic competition of extractables and/or titratable soluble against the insoluble polymer matrix of the superabsorbent fibers. Furthermore, extractables and/or titratable soluble can increase the viscosity of the surrounding liquid and this way can reduce the liquid flow in and the liquid absorption by the absorbent core.

Once the extractables and titratable soluble leave the network of the superabsorbent fibers during swelling, extractables and titratable soluble, especially extractable non-crosslinked polymers, can negatively impact capacity.

This happens on two accounts. While the first aspect, namely osmotic behavior, is especially reflected by the titratable soluble as determined by the Titratable Soluble Test Method set out below, the second aspect is better reflected by the amount of extractables as determined by the Amount of Extractables Test Method below.

Firstly, titratable soluble such as extracted non-crosslinked polyelectrolyte polymers, by being a charged polymers, increase the ionic strength of and the charge density in the liquid outside the superabsorbent fiber, which decreases the osmotic pressure and therefore the capacity of the superabsorbent fibers. Similarly, charged monomers and charged oligomers increase the ionic strength of and the charge density in the liquid outside the superabsorbent fiber, thus decreasing the osmotic pressure and therefore the capacity of the superabsorbent fibers. This drawback associated with titratable soluble is determined by the Titratable Soluble Test Method.

Secondly, by migrating out of the superabsorbent fibers, the extracted polymer decreases the active mass of swellable polymer. This does not only apply for charged extracted substances but for all extracted substances, i.e. also those which are neutral. At the same time, inherently, extractables, as not being connected to the network, does not contribute to mechanical strength of the superabsorbent fiber network. Therefore, extractables negatively impact both capacity and mechanical strength. Extractables, especially extractable non-crosslinked polymers, can negatively impact the liquid flow in a porous matrix such as a nonwoven web, by increasing the viscosity of the liquid. This slows down the transport of liquid in the nonwoven web such as the nonwoven web with superabsorbent fibers and leads to insufficient acquisition rates of the absorbent core. The test method below to measure the amount of extractables, does not only determine charged extracted substances but also determines neutral extracted substances, thus better reflecting the drawbacks of substances "escaping" from the superabsorbent fibers, which are set out in this paragraph.

Hence, the superabsorbent fibers comprised by the nonwoven web(s) of the absorbent core may have an amount of extractables of less than 20 weight-%, or less than 15 weight-%, or less than 12 weight-%, or less than 10 weight-% based on the total weight of the superabsorbent fibers according to the Extractables Test Method set out herein. Alternatively or in addition, the superabsorbent fibers may have an amount of titratable soluble of less than 20%, or less than 18%, or less than 15%, or less than 12%, or less than 10%, or less than 8%, or less than 6%, or less than 4% according to the Titratable Soluble Test Method set out herein.

The amount of extractables and the amount of titratable soluble can, for example, be reduced chemically, by crosslinking the extractables (e.g. loose monomers, oligomers and polymers) to the polymer network. For cross-linking, a crosslinking molecule or unit (i.e. functional part of a molecule) is provided under conditions that enable the formation of a covalent bond between the extractable and the polymer network via the crosslinking molecule or unit, e.g. by heat, UV light. The cross-linking molecule may be added to the polymer, or it may be an integral part of the polymer (e.g. part of the polymer chain). For superabsorbent polymer particles, it is also known to physically crosslink the extractables, e.g. by increasing the entanglement within the polymer network. Thereby, extractables are more efficiently "trapped" in the network.

Notably, typical extractables of superabsorbent fibers are not the same as extractables from superabsorbent polymer particles. Most commercially used superabsorbent polymer particles in disposable absorbent articles are made of cross-linked polyacrylic acid formed of acrylic acid monomers with relatively low amounts of co-monomers (i.e. other monomers than acrylic acid). In comparison, the superabsorbent fibers are typically formed of polymers with a more diverse combination of monomers.

The superabsorbent fibers may have a capacity of at least 7 g/g, or at least 8 g/g, or at least 10 g/g, or at least 12 g/g, or at least 15 g/g, or at least 18 g/g, or at least 20 g/g as measured according to the Centrifuge Retention Capacity test set out herein.

As used herein, the term "superabsorbent" refers to a water-swellable, water-insoluble material capable, under the most favorable conditions, of absorbing at least about 7, desirably of about 10, or about 15 times its weight in saline as measured according to the Centrifuge Retention Capacity test set out herein. Synthetic materials suitable for use as superabsorbent fibers of the present invention may be synthetic hydrogel polymers. Such polymers include, but are not limited to, alkali metal salts of polyacrylic acids, or alkali metal salts of polymers of monomeric groups e.g. comprised of/consisting of methyl (meth) acrylate, ethyl (meth) acrylate 2-ethyl hexyl (meth) acrylate, or polyacrylamides, polyvinyl alcohol, ethylene maleic anhydride copolymers, polyvinyl ethers, hydroxypropylcellulose, polyvinlmorpholinone, and polymers and copolymers of vinyl sulfonic acid, polyacrylates, polyacrylamides, polyvinyl amines, polyallylamines, polyvinylpyrridine, and the like. Other suitable polymers include hydrolyzed acrylonitrile grafted starch, acrylic acid grafted starch, and isobutylene maleic anhydride copolymers and mixtures thereof. The hydrogel polymers are crosslinked to render the material substantially water insoluble.

Preferred monomers for polymerization for making superabsorbent fibers are methyl (meth) acrylate, and/or monomers comprising a hydroxylic group, e.g. hydroxyalkyl (meth) acrylates, e.g. hydroxyethyl methacrylate, tripropyleneglycol mono acrylate, 5 glyceryl monoacrylate etc. The hydrogel polymers can comprise/consist of one kind of monomer, or preferably of two kinds of monomers or more preferably of three or more kinds of monomers. The monomers may be in a ratio such that the monomer of the third lowest amount (by weight %) to the monomer of highest amount (by weight %) is at least 1%, or at least 2% or at least 3.5% or at least 5% or at least 10%. In case the monomer is applied in a charged form (anionic or cationic), the weight without the counterion (e.g. sodium cation in case of sodium methacrylate) i.e. the weight of the neutral form is considered.

The superabsorbent fibers may comprise one or more superabsorbent materials in the form of a salt, such as sodium salt, potassium salt, ammonium salt or the like, of a cross-linked polymer.

As meant herein, if the superabsorbent fibers are made of a combination of two or more different monomers, such as a combination of three or more different monomers, the difference in monomer does not include the salt of a monomer. Thus, if a superabsorbent fiber is made of a combination of three different monomers, this includes the three monomers and the salt form of the three monomers.

The superabsorbent fibers can be made by a number of methods known to those skilled in the art. Superabsorbent fibers have been known in the art for decades. Patents describing such fibers and various methods to make them include U.S. Pat. Nos. 5,026,784; 5,151,465; 4,880,868; 4,743,244; 4,616,063; 4,705,773; 4,731,067; 4,731,067; 4,743,244; 4,788,237; 4,813,945; 5,280,079; 5,147,956; 4,980,434; 4,962,172; 4,997,714; 4,861,539; 4,366,206; 9,725,827; WO 2020/105529; EP 3,342,787; and U.S. Pat. No. 10,697,092. Despite the relatively large number of patents and patent applications related to superabsorbent fibers, the commercial use of such fibers in absorbent articles has hitherto been very limited.

Absorbent Core

The absorbent core of the present invention comprises one or more nonwoven webs with superabsorbent fibers. Each of the nonwoven webs comprises at least 80 weight-%, or at least 85 weight-%, or at least 90 weight-%, or at least 95 weight-% of superabsorbent fibers based on the total weight of the respective nonwoven web (herein collectively referred to as "nonwoven web with superabsorbent fibers"). The absorbent core as a whole comprises at least 60 weight-%, or at least 70 weight-%, or at least 75 weight-%, or at least 80 weight-%, or at least 90 weight-%, or at least 95 weight-%, or at least 98 weight-% of the superabsorbent fibers based on the total weight of the absorbent core.

Each of the nonwoven webs has a capacity of at least 7 g/g, or at least 8 g/g, or at least 10 g/g, or at least 12 g/g, or at least 15 g/g, or at least 18 g/g, or at least 20 g/g as measured according to the Centrifuge Retention Capacity test set out herein.

Each of the nonwoven webs comprising at least 80 weight-% or at least 85 weight-%, or at least 90 weight-%, or at least 95 weight-%, or at least 98 weight-% of superabsorbent fibers based on the total weight of the respective nonwoven web, may have a basis weight of at least 80 g/m², or at least 100 g/m², or at least 150 g/m², or at least 200 g/m².

The nonwoven webs with superabsorbent fibers may comprise less than 20 weight-%, or less than 15 weight-%, or less than 10 weight-%, or less than 5 weight-% of other material than superabsorbent fibers. Such "other material" may be non-superabsorbent fibers, adhesive, superabsorbent polymer particles, or the like. Non-superabsorbent fibers may be natural fibers, such as cellulose fibers and/or cotton fibers, or may be synthetic fibers, such as polyolefin fibers or polyethylene fibers. Suitable polyolefin fibers may be polyethylene fibers and/or polypropylene fibers. The synthetic fibers may be continuous fibers, such as spunbond fibers and/or meltblown fibers, or, preferably, may be staple fibers which have an average fiber length of 100 mm or less (e.g. from 20 mm to 80 mm, or from 25 mm to 55 mm).

It is preferred that the absorbent core comprises less than 20 weight-% of superabsorbent polymer particles.

The absorbent core of the present invention may comprise of one or more nonwoven web(s) with superabsorbent fibers which comprise less than 20 weight-% of other material than superabsorbent fibers, and may further comprise one or more nonwoven web(s) which consist of superabsorbent fibers.

The absorbent core may comprise additional layers, such as nonwoven webs not comprising superabsorbent fibers, or film layers (e.g. apertured films), or tissue layers made of wet-laid pulp. Such additional layers may be placed in between two of the nonwoven webs with superabsorbent fibers. The additional layers may each have a basis weight of not more than 20 g/m², or not more than 18 g/m², or not more than 15 g/m². The total basis weight of the additional layers may not be more than 50 g/m², or may not be more than 40 g/m², or may not be more than 25 g/m².

The absorbent core may have one additional layer as a top layer and forming the surface of the absorbent core which provided towards wearer when the absorbent core is incorporated in an absorbent article and the absorbent article is in use. Alternatively or in addition, the absorbent core may have one additional layer as a bottom layer and forming the surface of the absorbent core which provided away from the wearer when the absorbent core is incorporated in an absorbent article and the absorbent article is in use.

The absorbent core may not comprise additional layers other than the top layer and/or the bottom layer.

Alternatively, the absorbent core may not comprise any additional layers.

The absorbent core as a whole comprises at least 60 weight-%, or at least 70 weight-%, or at least 75 weight-%, or at least 80 weight-%, or at least 90 weight-%, or at least 95 weight-%, or at least 98 weight-% of the superabsorbent fibers based on the total weight of the absorbent core. The absorbent core as a whole may have a capacity of at least 7 g/g, or at least 8 g/g, or at least 10 g/g, or at least 12 g/g, or at least 15 g/g, or at least 18 g/g, or at least 20 g/g as measured according to the Centrifuge Retention Capacity test set out herein.

The superabsorbent fibers comprised by the absorbent core may have a capacity of at least 7 g/g, or at least 8 g/g, or at least 10 g/g, or at least 12 g/g, or at least 15 g/g, or at least 18 g/g, or at least 20 g/g as measured according to the Centrifuge Retention Capacity test set out herein.

If the absorbent core comprises more than one nonwoven web with superabsorbent fibers, the webs may be attached to each other e.g. by adhesive. To reduce the overall amount of adhesive in order to reduce a possible negative impact to the absorbent properties and to the softness of the absorbent core, the amount of adhesive should be relatively low. Also, the adhesive may only be applied intermittently.

If the absorbent core comprises additional layers, i.e. layers not comprising superabsorbent fibers, these additional layers may also be adhesively attached to each other and/or to the nonwoven webs with superabsorbent fibers. Similar to the above, to reduce the overall amount of adhesive in order to reduce a possible negative impact to the absorbent properties and to the softness of the absorbent core, the amount of adhesive should be relatively low. Also, the adhesive may only be applied intermittently.

The absorbent core has a longitudinal direction with a longitudinal axis and a transverse direction with a transverse axis. The longitudinal axis is perpendicular to the transverse axis. Being incorporated into an absorbent article, the longitudinal direction of the absorbent core may be substantially parallel, or may be parallel with the longitudinal direction of the absorbent article and the transverse direction of the absorbent core may be substantially parallel or may be parallel with the transverse direction of the absorbent article.

If the absorbent core comprises more than one nonwoven web with superabsorbent fibers, the webs may be arranged on top of one another (relative to the thickness direction of the absorbent core which is perpendicular to the longitudinal and transverse direction) and/or may be arranged next to each other. The more than one nonwoven webs with superabsorbent fibers may differ from each other in shape and/or size.

If the nonwoven webs are arranged next to each other, they may be arranged next to each other with regard to the longitudinal direction and/or with regard to the transverse direction of the absorbent core. Such arrangement allows the creation of channels within the absorbent core, wherein a channel is formed at the boundaries between neighboring nonwoven webs with superabsorbent fibers that are arranged next to each other. The boundaries between the neighboring webs with superabsorbent fibers may be shaped such that curved channels are formed which extend in longitudinal direction of the absorbent core across the transverse axis and curved inwardly towards the longitudinal axis.

The absorbent core may comprise a central nonwoven web with superabsorbent fibers that extends along the longitudinal direction and one nonwoven web with superabsorbent fibers may be provided on each side of the central nonwoven web along the longitudinal direction. The central nonwoven web may have a higher basis weight than each of the nonwoven webs provided on the sides. Alternatively or in addition, more than one central nonwoven web with superabsorbent fibers may be provided, such that these nonwoven webs with superabsorbent fibers are arranged on top of one another. Thereby, varying basis weight can be provided in the absorbent core to provide more tailor-made absorbent capacity in the various areas of the absorbent core.

Preferably, the nonwoven web with superabsorbent fibers is a carded nonwoven web. The superabsorbent fibers, as well as other fibers optionally comprised by the nonwoven web, may have a length of less than 200 mm, or less than 150 mm, or less than 100 mm.

The absorbent core may have a basis weight of from 20 to 1000 g/m², or from 150 g/m² to 800 g/m², or from 200 g/m² to 600 g/m². If the basis weight varies across the area of the absorbent core, the basis weight is the average basis weight.

The absorbent core as a whole, or one of the nonwoven webs, or all of the nonwoven webs with superabsorbent fibers comprised by the absorbent core may have channels. Channels are areas within the absorbent core and/or within the nonwoven web(s) with superabsorbent fibers, where no absorbent material (or no material at all) is provided. Hence, channels form gaps in the absorbent core and/or nonwoven web(s) with superabsorbent fibers. The absorbent core and/or nonwoven web(s) with superabsorbent fibers may comprise two or more channels. The channels may extend along the longitudinal direction of the absorbent core and/or nonwoven web(s) with superabsorbent fibers (i.e. such that they extend along the longitudinal direction of the absorbent article which may comprise the absorbent core). The channels may have a length to width ratio of at least 10 to 1. The channels may have a width of at least 1 mm, or at least 2 mm. The channels may have a width of not more than 30 mm, or not more than 25 mm. The channels may have a length of at least 10 mm, or at least 20 mm, or at least 30 mm, or at least 40 mm.

The basis weight is determined for the complete area surrounded by the outer perimeter of the absorbent core. If one or more, or all of the nonwoven webs comprised by the absorbent core, is facilitated with channels, cavities or other areas where no material is provided, then these areas where no material is provided, is taken into consideration and included in the determination of the area of the absorbent core. If the absorbent core is configured by providing two or more nonwoven webs next to each other within the plane of the absorbent core (which is perpendicular to the longitudinal and transverse axis of the absorbent core), then the perimeter of the absorbent core is taken along the outermost edges of the complete absorbent core, i.e. including all nonwoven webs of the absorbent core.

The appropriate basis weight of the absorbent core depends on the absorbent article in which it is intended to be used.

If the absorbent core is provided in a diaper or pant (such as a diaper or pant for babies, toddlers or adults), the basis weight of the absorbent core may be at least 100 g/m$^2$, or at least 150 g/m$^2$, or at least 200 g/m$^2$, or at least 300 g/m$^2$. In such absorbent articles, the basis weight of the absorbent core may be not more than 1000 g/m$^2$, or not more than 800 g/m$^2$, or not more than 600 g/m$^2$.

If the absorbent core is provided in an absorbent article for feminine hygiene, such as a sanitary napkin, the basis weight of the absorbent core may be at least 20 g/m$^2$, or at least 25 g/m$^2$, or at least 30 g/m$^2$, or at least 40 g/m$^2$. In such absorbent articles, the basis weight of the absorbent core may be not more than 200 g/m$^2$, or not more than 150 g/m$^2$.

The absorbent core (for all absorbent articles) may have a dry caliper of from 1 to 20 mm, or from 2 mm to 10 mm, as measured with the test method described herein.

The absorbent core may have a length of at least 200 mm as measured along the longitudinal axis of the absorbent core.

The absorbent core may have a width of not more than 170 mm. If the width of the absorbent core varies along the longitudinal axis, the maximum width of the absorbent core may not be more than 170 mm.

The absorbent core of the present invention may have any suitable shape such as rectangular, hourglass shaped, dog bone shaped, and oval.

Surfactant Treatment

The superabsorbent fibers of the nonwoven web with superabsorbent fibers comprise a surfactant, i.e. they may be treated with one or more surfactant(s), or the surfactant may be added to the superabsorbent fiber during fiber making as explained in more detail in the following. The surfactants may be non-ionic, anionic or cationic. It is believed that non-ionic surfactants may be preferable for use in the present invention. The surfactants may be ethoxylated alcohols or ethoxylated fatty acids, such as non-ionic ethoxylated alcohols or ethoxylated fatty acids. Suitable surfactants are, for example, fatty alcohol polyethyleneglycol ether, ethoxylated fatty acids, polyglycol ether, modified polyethyleneimine (PEI), siloxane polyalkyleneoxide copolymer, polyalkylenoxide-modified polydimethylsiloxane, ethoxylated C12 alcohols, ethoxylated C13 alcohols, ethoxylated C14 alcohols, ethoxylated C12-C14 alcohols, and mixtures thereof.

Especially suitable surfactants include Hedipin CFA/100 available from W. Kolb AG, PST-N (anionic) available from Schill+Seilacher GmbH, Germany, Marlipal 24/99 and LIALET 12 3-8 available from Sasol Performance Chemicals, Italy, Tergitol Type 15-S-7 available from Sigma Aldrich, Duron OS 1547 and Duron OF 401 available from CHT Germany GmbH, Nuwet 237 and Nuwet 550 available from Momentive Performance Materials Inc., USA, and Stantex K1342, Stantex S6887 and STantex S6327 available from Pulcra Chemicals, Germany.

The superabsorbent fibers and nonwoven webs with the superabsorbent fibers and comprised by the absorbent core of the present invention, may be treated with a combination of several different surfactants.

The superabsorbent fibers can be treated with the surfactant before or after the superabsorbent fibers have been converted into a nonwoven web. Preferably, the superabsorbent fibers are treated with the surfactant after the superabsorbent fibers have been converted into a nonwoven web.

More preferably, the nonwoven web as a whole is treated with surfactant after the superabsorbent fibers have been converted into a nonwoven web, i.e. not only the superabsorbent fibers but also other material that may be comprised by the nonwoven webs with superabsorbent fibers. This can be beneficial as the hydrophilicity of the other material (which may initially be rather hydrophobic) can be improved together with the treatment of the superabsorbent fibers, hence, simplifying the manufacturing process.

Treatment with surfactant does, however, not necessarily mean that each and every fiber (superabsorbent fibers and optional other material) is treated with surfactant as long as at least one or both surfaces of the nonwoven web are surfactant treated, especially as, due to the nature of a nonwoven web, a treatment applied on a surface will also penetrate into the nonwoven web to some extent. The treatment with surfactant can be done by any known method known in the art. For example, the surfactant can be applied by spraying the surfactant on the superabsorbent fibers or on the nonwoven web with the superabsorbent fibers. If the surfactant is applied on the nonwoven web with the superabsorbent fibers by spraying, the surfactant may be sprayed on one or both surface areas of the nonwoven web. If the nonwoven web has a rather high caliper and/or basis weight, it may be preferable to spray on both surface areas of the nonwoven web to ensure sufficient treatment of the superabsorbent fibers with the surfactant.

Alternatively to spraying, the surfactant can also be applied by dip-coating. For dip-coating, the superabsorbent fibers (before formation of the nonwoven web) or the nonwoven web with the superabsorbent fibers are/is dipped into a reservoir with the surfactant.

Alternatively, the surfactant may be applied via coating (so-called "kiss-roll").

In a further alternative, the surfactant may be added to the polymer mixture during the method of making the superabsorbent fibers. Thereby, the surfactant is comprised by the surface of the superabsorbent fiber as well as within the fiber.

If the superabsorbent fibers are surfactant treated after conversion into the nonwoven web and, further, if the surfactant treatment is carried out by spraying surfactant on one or both of the nonwoven surfaces, the absorbent core may be formed of more than one nonwoven web with superabsorbent fibers. Thereby, the overall area which is surfactant treated can be increased for an absorbent core of similar overall basis weight of the nonwoven with superabsorbent fibers.

If the nonwoven web with superabsorbent fibers is surfactant treated by, e.g. passing the nonwoven web through a container that contains the surfactant (e.g. in aqueous solution) and thus soaking the complete nonwoven web with surfactant, it is less critical if the absorbent core comprises more than one nonwoven web with superabsorbent fibers.

The superabsorbent fibers can be essentially free of surfactant before being converted into the nonwoven web such that surfactant treatment is only carried out for the nonwoven web with superabsorbent fibers.

The superabsorbent fibers may also comprise one or more surfactant(s) that has been added during the making of the superabsorbent fibers and, in addition, such superabsorbent fibers may be treated with one or more surfactant(s) after formation, e.g. by spraying or dip-coating.

The one or more nonwoven webs with superabsorbent fibers and comprised by the absorbent core may comprise at least 0.001 weight-%, or at least 0.01 weight-%, or at least 0.02 weight-%, or at least 0.05, or at least 0.10 weight-%, or at least 0.20 to 0.80 weight-% of surfactant based on the weight of the respective nonwoven web with superabsorbent fibers. The one or more nonwoven webs with superabsorbent fibers and comprised by the absorbent core may not comprise more than 1.00 weight-%, or not more than 0.80 weight-% of surfactant based on the weight of the respective nonwoven web with superabsorbent fibers. Amounts of more than 1.00 weight-% are not expedient as the functionality of the surfactant in increasing the hydrophilicity of the superabsorbent fibers and nonwoven webs reaches a plateau such that a further increase in the amount leads to little or no further improvement, whereas further increasing the amount results in unnecessary increase in cost and a higher risk of wash off of the surfactant during use of the absorbent core/absorbent article. If the one or more nonwoven webs with superabsorbent fibers and comprised by the absorbent core comprises more than one surfactant, the amount in weight-% refers to the total amount of all surfactants. The weight-% relates to the surfactant as such, i.e. if the surfactant is applied in a solvent, the amount of solvent is not taken into consideration for determining the weight-%.

The treatment of the superabsorbent fibers and/or nonwoven web with superabsorbent fibers with surfactants enables fast fluid acquisition times of the absorbent core, as the contact angle between liquid and superabsorbent fibers can be considerably reduced, so the wetting of the superabsorbent fibers can be considerably improved. The absorbent core of the present invention may have an acquisition time of a) less than 120 seconds, or less than 100 seconds after the 1st gush, and b) less than 300 seconds, or less than 200 seconds after the 2nd gush, and c) less than 500 seconds, or less than 300 seconds after the 3rd gush as measured according to the Modified Fluid Acquisition test method set out below.

Method of Making the Absorbent Core

The absorbent core as described and comprising the superabsorbent fibers described above may be made by a method comprising the following steps:

a) providing superabsorbent fibers; and b) converting the superabsorbent fibers into a continuous nonwoven web; and c) (i) forming a continuous absorbent core which comprises one or more separate nonwoven webs with superabsorbent fibers and cutting the continuous absorbent core into separate absorbent cores; or (ii) cutting the continuous nonwoven web with superabsorbent fibers into separate nonwoven webs with superabsorbent fibers and forming an absorbent core which comprises one or more of the separate nonwoven webs with superabsorbent fibers.

One or more surfactant(s) is/are provided on and/or inside the superabsorbent fibers, and/or on the continuous nonwoven web, and/or on the separate sheets of nonwoven web.

The nonwoven web(s) have an amount of extractables of less than 20 weight-% based on the total weight of the nonwoven web(s), according to the Extractable Test Method set out herein, and/or wherein the nonwoven web(s) have an amount of titratable soluble of less than 20% according to the Titratable Soluble Test Method set out herein.

The absorbent core may consist of only one nonwoven web with superabsorbent fibers.

If the absorbent core comprises more than one nonwoven web with superabsorbent fibers, the method may comprise the following steps which are carried out after method step b):

assembling two or more continuous nonwoven webs with superabsorbent fibers such that they are in a face to face relationship on top of one another, and/or assembling two or more continuous nonwoven webs next to each other in a side-by-side relationship; and/or assembling one or more of the separate sheets of nonwoven webs into the absorbent core.

Hence, two or more nonwoven webs may be assembled while the nonwoven web is still in its continuous configuration such that two or more continuous nonwoven webs with superabsorbent fibers are assembled rather than separate nonwoven webs with superabsorbent fibers. Alternatively or in addition, two or more nonwoven webs may be assembled after the continuous nonwoven web has been cut into separate nonwoven webs.

For example, two or more (such as two or three) continuous nonwoven webs with superabsorbent fibers may be assembled in a face to face relationship on top of one another and, subsequently, the assembled continuous nonwoven webs with superabsorbent fibers may be cut into separate nonwoven webs, wherein two or more (such as two or three) separate nonwoven webs are in a face to face relationship on top of one another due to their previous assembly as continuous nonwoven webs with superabsorbent fibers.

These assembled nonwoven webs with superabsorbent fibers may form the absorbent core.

Alternatively, one or more additional nonwoven web(s) with superabsorbent fibers may be joined to these assembled nonwoven webs with superabsorbent fibers, e.g. by providing the one or more additional nonwoven web(s) in a face to face relationship with the assembled nonwoven webs; and/or by providing the one or more additional nonwoven web(s) next to each other in a side-by-side relationship with the assembled nonwoven webs to form the absorbent core.

If the absorbent core comprises additional layers in addition to the nonwoven web(s) with superabsorbent fibers (as explained in more detail above, the description being equally applicable to the method of the present invention), the additional layers may be provided as additional continuous layers while the nonwoven web(s) with superabsorbent fibers is/are still in their continuous configuration, or may be provided when the nonwoven web(s) with superabsorbent fibers is/are cut into separate nonwoven webs.

For example, two additional layers of nonwoven webs having no superabsorbent fibers may be provided such that they form the outer layers of the absorbent core, with one additional layer on each surface of the absorbent core.

Additional layers may also be provided in between two nonwoven webs with superabsorbent fibers which are provided on top of one another.

Also, one or more additional layer may be provided as continuous additional layers to separate, cut nonwoven webs with superabsorbent fibers. For example, one or more cut nonwoven web(s) with superabsorbent fibers may be laid down on a continuous additional layer (such as a nonwoven web having no superabsorbent fibers) in a spaced relationship, i.e. so that there is a gap (in machine direction) between neighboring nonwoven webs with superabsorbent fibers. A further continuous additional layer may subsequently be provided on top of spaced nonwoven webs with superabsorbent fibers. Thereafter, the continuous additional layers are cut in the region where the nonwoven webs with superabsorbent fibers are spaced from one another in machine direction to provide absorbent cores.

The nonwoven web(s) with superabsorbent fibers may have an amount of extractables of less than 15 weight-%, or less than 12 weight-%, or less than 10 weight-% based on the total weight of the nonwoven web(s) with superabsorbent fibers, according to the Extractable test method set out herein, and/or the nonwoven web(s) with superabsorbent fibers may have an amount of titratable soluble of less than 18%, or less than 15%, or less than 12%, or less than 10%, or less than 8%, or less than 6%, or less than 4% according to the Titratable Soluble Test Method set out herein.

Moreover, the nonwoven webs with superabsorbent fibers have a capacity of at least 7 g/g as measured according to the Centrifuge Retention Capacity test set out herein. The nonwoven webs with superabsorbent fibers may have an amount of extractables of less than 15 weight-% based on the total weight of the respective nonwoven web with superabsorbent fibers.

Moreover, the absorbent core comprises at least 60 weight-%, or at least 70 weight-%, or at least 75 weight-%, or at least 80 weight-%, or at least 90 weight-%, or at least 95 weight-%, or at least 98 weight-% of the superabsorbent fibers based on the total weight of the absorbent core.

The method may further comprise the step of reducing the amount of extractables and reducing the amount of titratable soluble after the superabsorbent fibers have been converted into a coherent, self-sustaining nonwoven web. For example, the continuous nonwoven web provided in step b), the separate sheets of nonwoven web in step c) and/or the assembled absorbent core in step c) may be subjected to heating. Such heating may be carried out at a temperature of from 150° C. to 300° C., or from 180° C. to 240° C., or from 200 to 225° C., and may be carried out for 10 seconds to 30 min, or from 1 min to 15 min, or from 3 min to 10 min, or from 4 min to 8 min. The heating can be done by hot air via circulation heaters, electromagnetic irradiation (such as IR), or halogen heaters or the like.

Converting the superabsorbent fibers into a continuous nonwoven web means that the superabsorbent fibers are laid down on a moving belt or rotating drum to form a continuous nonwoven web. To ease fiber laydown, a vacuum may be applied beneath the belt or within the drum. The self-sustainability of the nonwoven web can be obtained by any means known in the art, such as entangling the fibers, e.g. by needle-punching, or by bonding the fibers adhesively, or with heat/and or pressure. A self-sustaining nonwoven web is a web which has sufficient integrity to not disintegrate and fall apart, e.g. when wound up in roll-form. Thereby, the continuous nonwoven web with the superabsorbent fibers may be manufactured at one location and being cut into separate sheets of nonwoven web and incorporated into an absorbent core in another location.

The method further comprises providing a surfactant on and/or inside the superabsorbent fibers, and/or on the continuous nonwoven web, and/or on the separate sheets of nonwoven web. This may be carried out before and/or after the superabsorbent fibers are converted into the nonwoven web. It may be facilitated before and/or after the continuous web are cut into separate sheets of nonwoven web.

Alternatively or in addition, the superabsorbent fibers provided in method step a) may comprise a surfactant which has been added during manufacture of the superabsorbent fibers such that the surfactant is comprised on the surface of the superabsorbent fibers as well as inside the superabsorbent fibers.

Alternatively, the superabsorbent fibers provided in method step a) may be essentially free of surfactant and the surfactant is only added at a later method step.

Still further alternatively, the superabsorbent fibers provided in method step a) comprise one or more surfactant(s) and are additionally treated with one or more surfactant(s) at a later method step.

The surfactant may be applied by any method known in the art, e.g. by spraying or dip-coating.

The surfactant is applied as solution with a solvent, the solvent may be less than 50 weight-%, less than 40 weight-%, less than 30 weight-%, less than 20 weight-% based on the total amount of solution. The surfactant can be applied in an aqueous or organic solvent.

The surfactant may be a liquid surfactant which is applied to the superabsorbent fibers without using any solvent or with using only very small amounts of solvent, such as less than 10 weight-%, or less than 5 weight-%, or less than 2 weight-% based on the total amount of solution. Such application has the advantage that little or no solvent needs to be removed after application of the surfactant (as removal can be time and/or energy consuming). Also, there is a low or no risk of residual solvent left on the fibers even after removal of the solvent.

The assembly of the one or more nonwoven webs in method step c) may comprise providing at least two of the nonwoven webs with superabsorbent fibers and arrange them in a face to face relationship such that all or portions of the absorbent core comprises more than one of the nonwoven web with superabsorbent fibers. Alternatively, or in addition, the assembly in method step c) may comprise arranging two or more nonwoven webs with superabsorbent fibers next to each other (instead of on top of one another).

If the assembly in method step c) comprises arranging two or more nonwoven webs with superabsorbent fibers next to each other, the two or more nonwoven webs may be arranged such that one or more channel(s) or cavities is formed at the boundaries between neighboring nonwoven webs.

The method may comprise a further step of incorporating the absorbent core into an absorbent article, such as a diaper and/or pant.

Absorbent Article

The absorbent core of the present invention may be comprised in an absorbent article.

Figure 2:
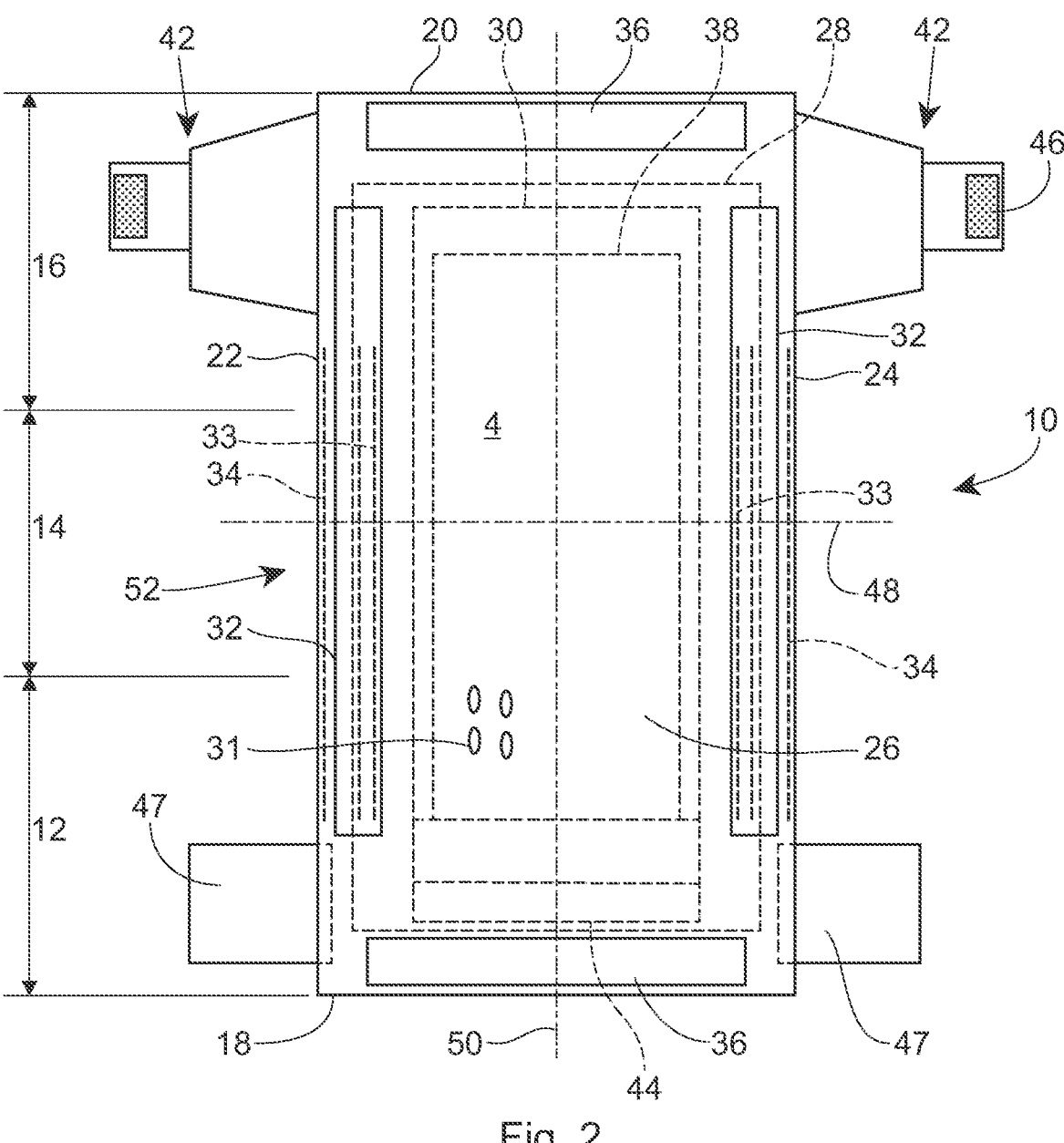
FIG. 2 is a plan view of the example absorbent article of FIG. 1, wearer-facing surface facing the viewer, in a flat laid-out state.
Figure 3:
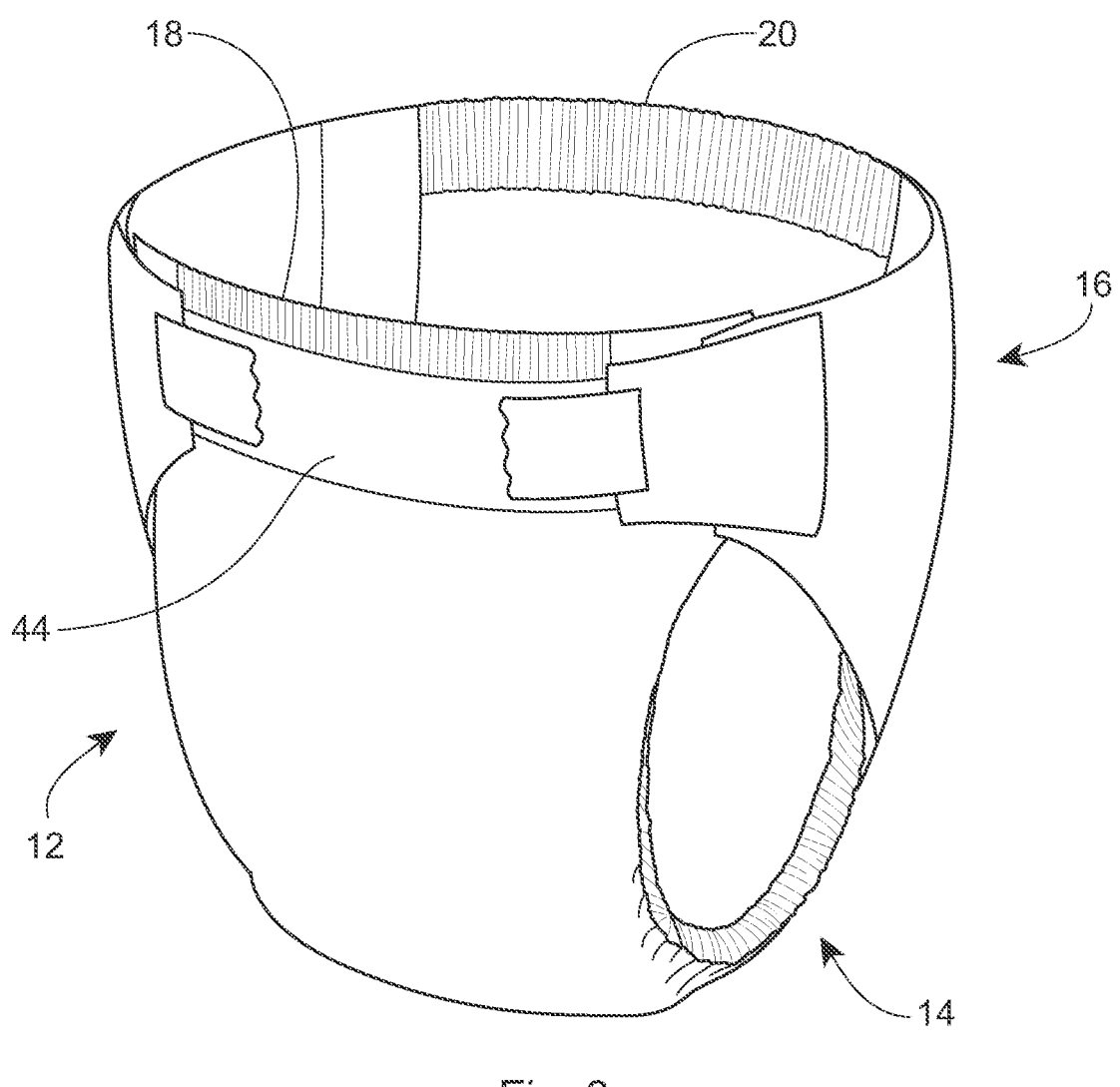
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plane view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front waist region 12 extends from a front waist edge towards the crotch region 14 and the back waist region 16 extends from a back waist edge towards the crotch region 14. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and the absorbent core 30 of the present invention positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. The absorbent articles of the present invention may, however, not comprise any acquisition material or materials 38. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12.

The absorbent article 10 may have a transverse axis 48 extending along a transverse direction and a longitudinal axis 50 extending along a longitudinal direction. The transverse axis 48 extends perpendicular to the central longitudinal axis 50. The front waist edge and the back waist edge extend parallel or substantially parallel to the transverse axis. "Substantially parallel" means that there may be a deviation of up to 10°, or up to 5°. If the front and/or back waist edge is curved, the deviation of up to 10°, or up to 5° is calculated for the tangent of the curvature. If more than one tangent can be determined (due to the kind of curvature), the tangent with the highest deviation is taken to calculate the angle of deviation. The front and back waist edge are preferably not wavy.

The absorbent article may have a total length measured along the longitudinal axis from the front waist edge and to the back waist edge. The front waist region, the back waist region, and the crotch each constitute ⅓ of the total length.

Figure 4:
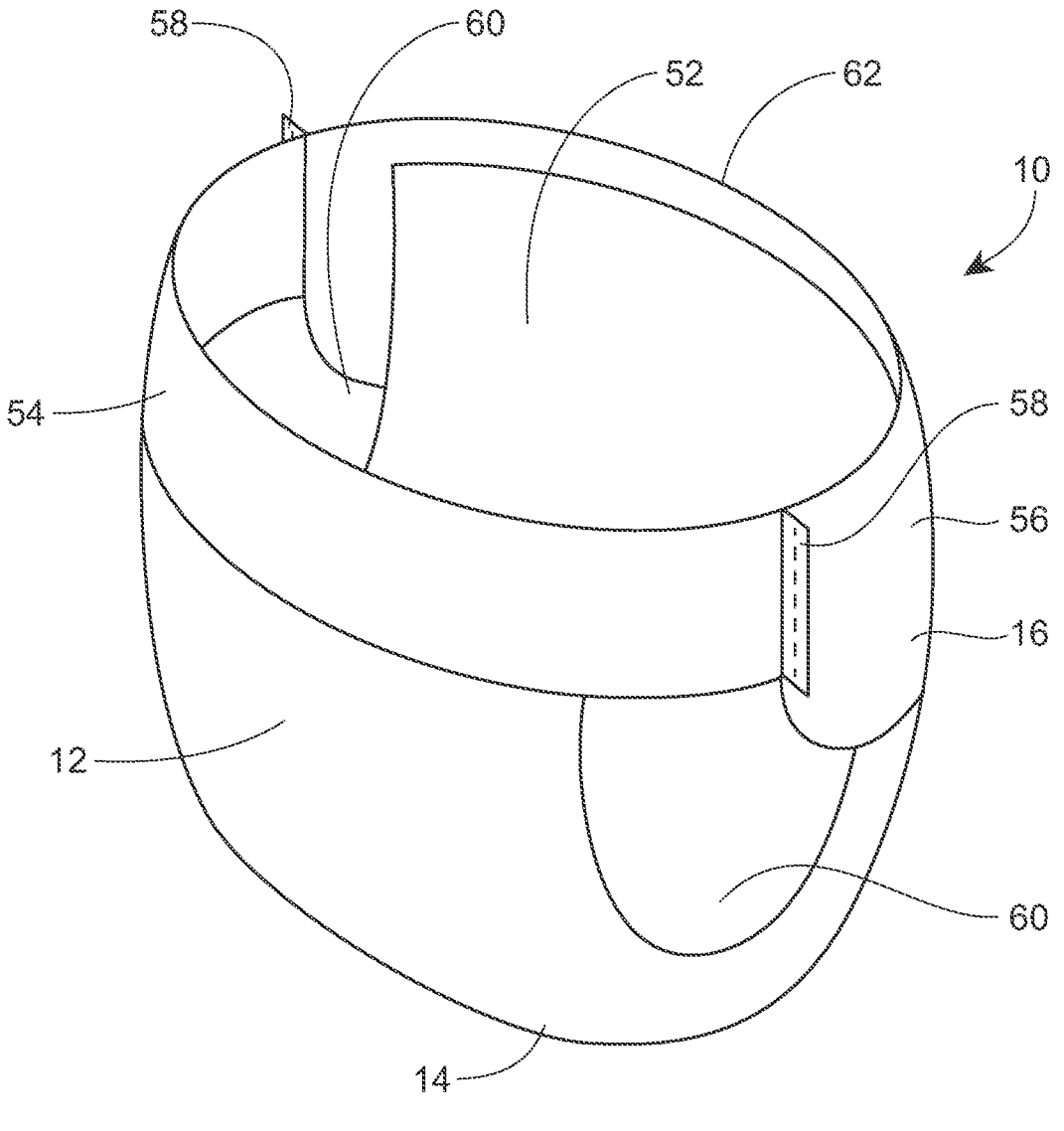
FIG. 4 is a front perspective view of an absorbent article in the form of a pant.
Figure 5:
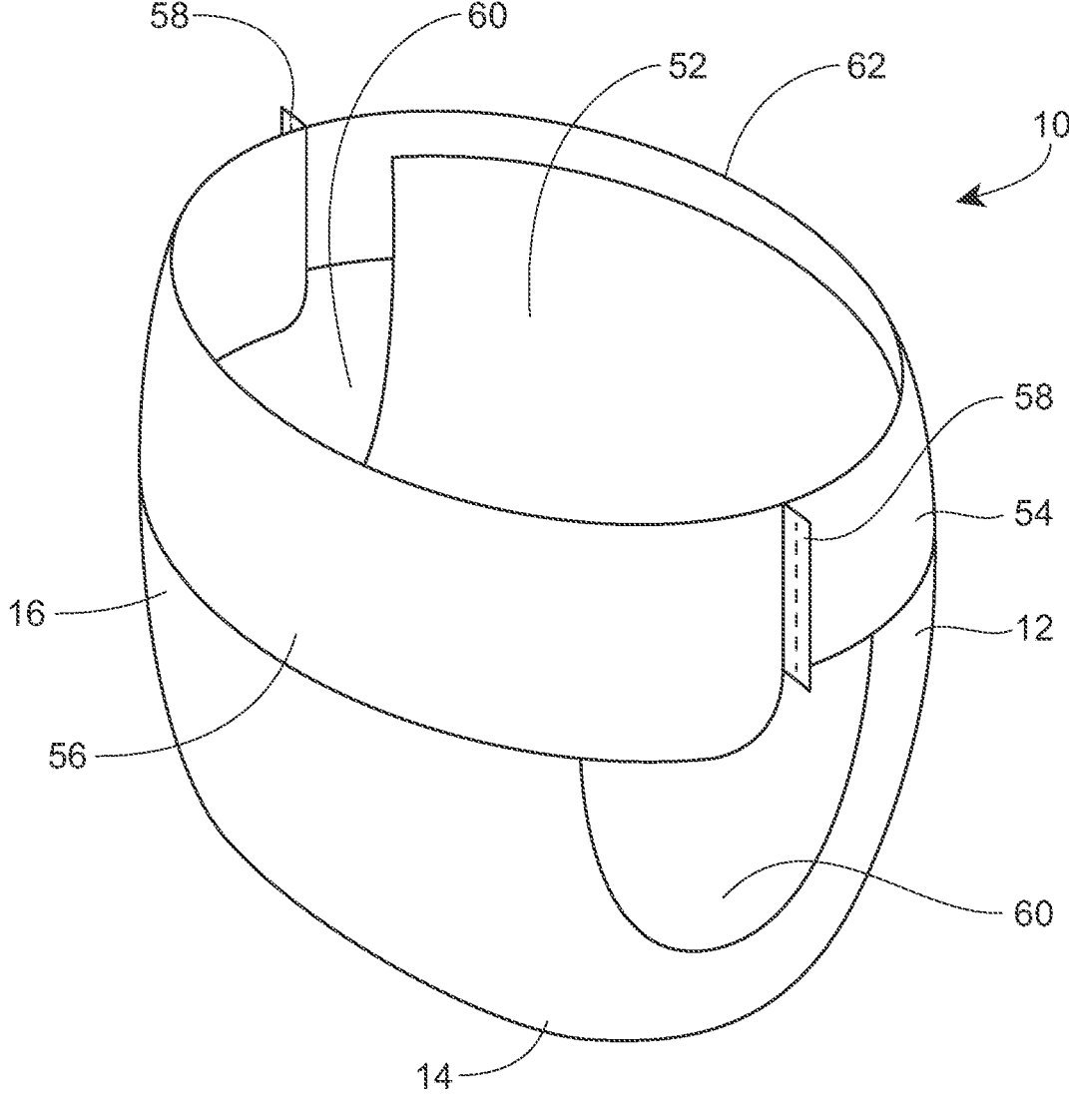
FIG. 5 is a rear perspective view of the absorbent article of FIG. 4.
Figure 6:
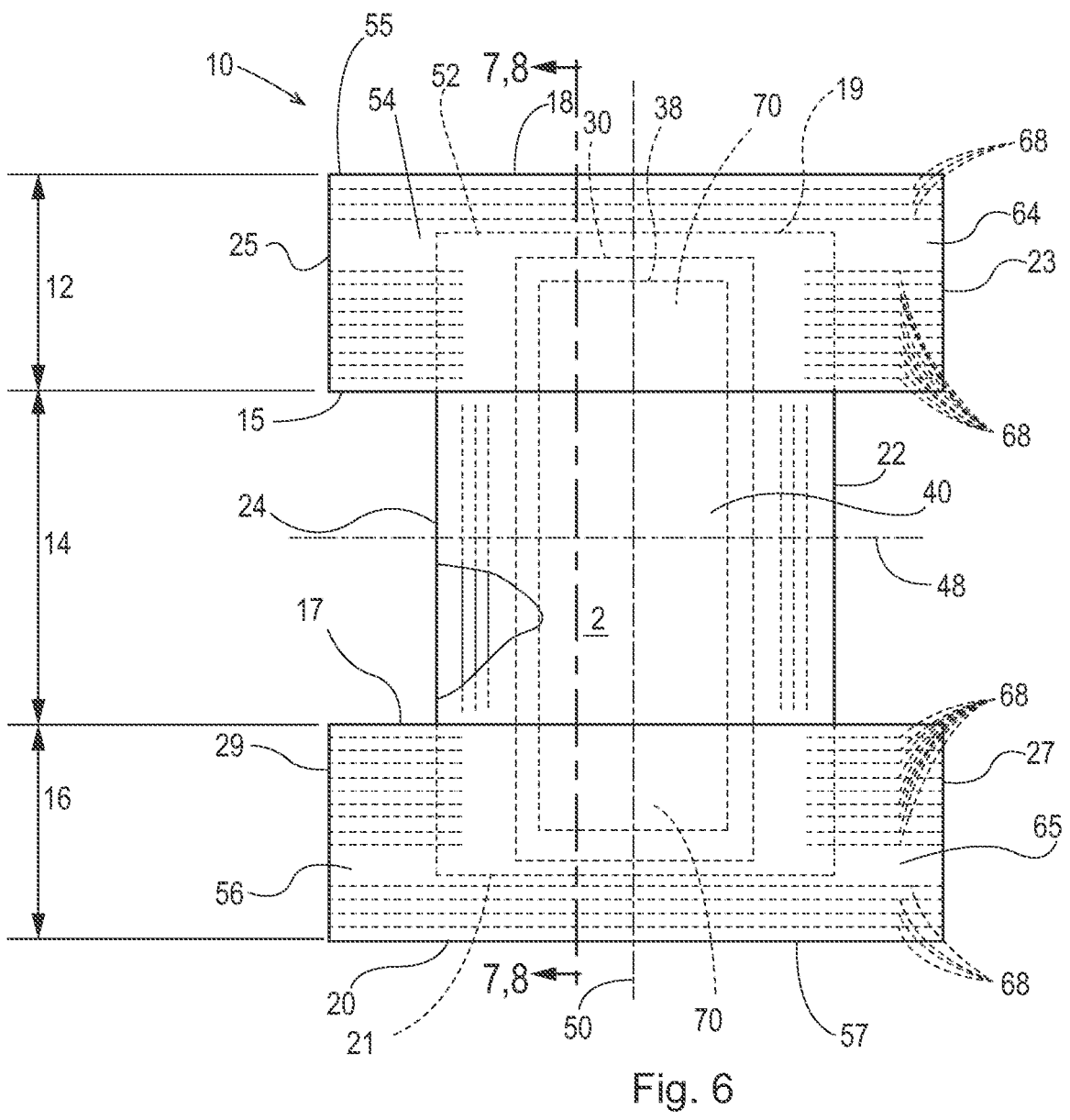
FIG. 6 is a plan view of the absorbent article of FIG. 4, laid flat, with a garment-facing surface facing the viewer.
Figure 7:
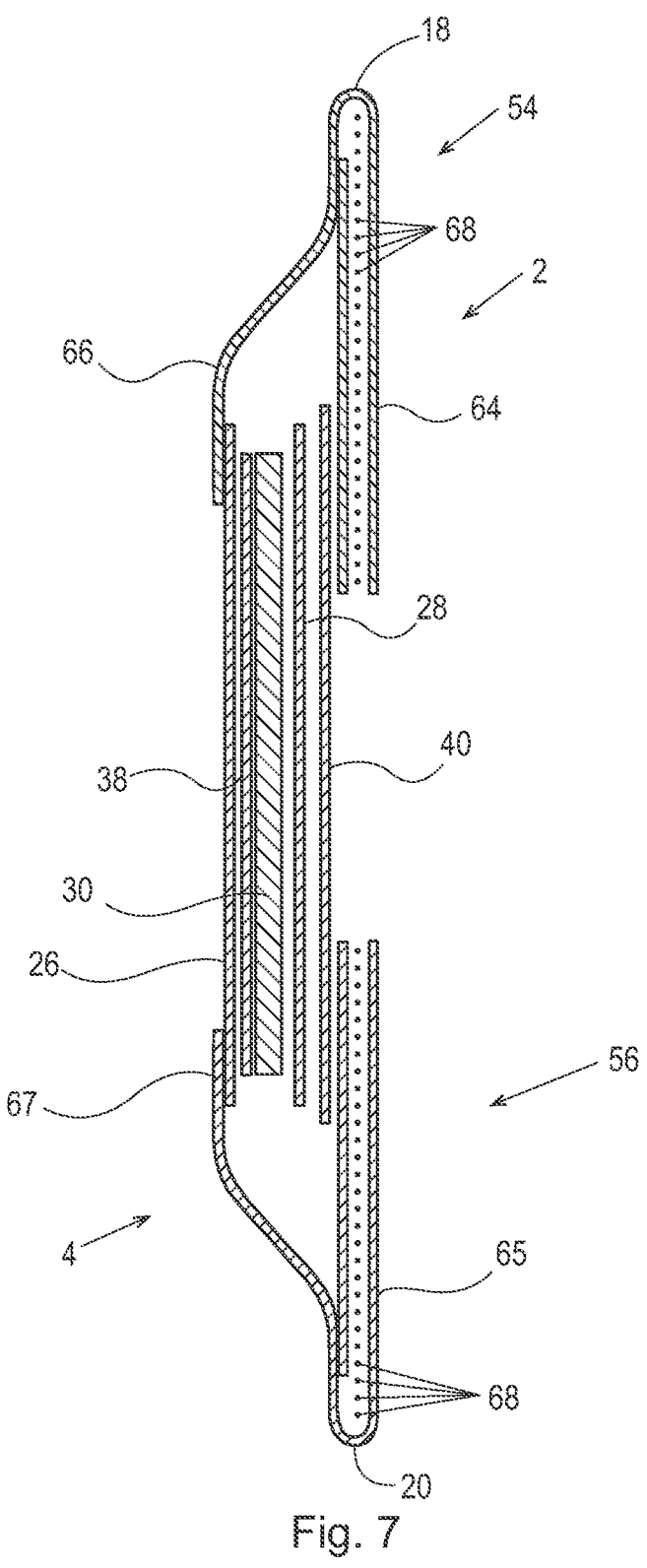
FIG. 7 is a cross-sectional view of the absorbent article taken about line 7-7 of FIG. 6.
Figure 8:
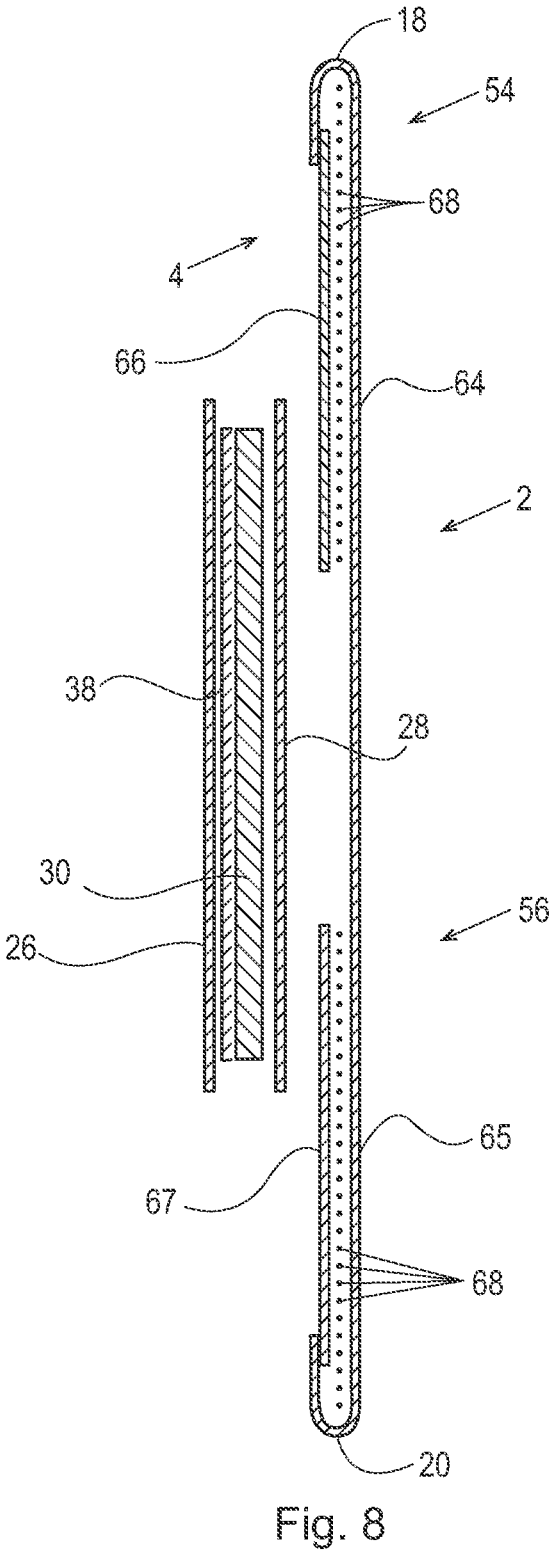
FIG. 8 is a cross-sectional view of the absorbent article taken about line 8-8 of FIG. 6.

The absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate alternative example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and the absorbent core 30 of the present invention disposed at least partially intermediate the topsheet 26 and the backsheet 28, and an optional (though not preferred) acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

In another form, the absorbent article may be an insert for use with a reusable outer cover. The insert may be disposable or reusable. The reusable outer cover may comprise a woven or other material and may be configured as a pant or a taped diaper. In the taped context, the reusable outer cover may comprise a fastening system used to join a front waist region of the reusable outer cover to a back waist region. The fastening system may comprise snaps, buttons, and/or hooks and loops, for example. The insert may comprise a liquid permeable topsheet, a liquid impermeable backsheet, and the absorbent core of the present invention positioned at least partially intermediate the topsheet and the backsheet. One or more acquisition and/or distribution materials may be positioned intermediate the topsheet and the absorbent core. The insert may comprise one or more pairs of leg cuffs and may be free of ears, side panels, and/or waistbands. In some instances, a nonwoven material may be positioned on a garment-facing side of the backsheet. A garment-facing surface of the insert may be attached to a wearer-facing surface of the reusable outer cover via adhesives, hook and loop fasteners, or other methods of joinder. An example insert and reusable outer cover system is disclosed in U.S. Pat. No. 9,011,402, issued on Apr. 21, 2015, to Roe et al. The insert or the reusable outer cover may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features. The outer cover material 40 may be a hydroentangled nonwoven material.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, the absorbent article may comprise an acquisition system. One or more acquisition materials 38 may be present at least partially intermediate the topsheet 26 and the absorbent core 30. If acquisition materials are provided, they are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels. The channels in the acquisition material may align or not align with channels in the absorbent core 30 as described above with reference to the absorbent core 30. In an example, a first acquisition material may comprise a nonwoven material and as second acquisition material may comprise a cross-linked cellulosic material.

If the absorbent article comprises an acquisition system, the absorbent article may comprise a topsheet and a backsheet, wherein the absorbent core is provided between the topsheet and the backsheet, and the acquisition system is provided between the absorbent core and the topsheet.

In such absorbent articles, the absorbent core and the acquisition system in conjunction may have an acquisition time of less than 120 seconds, or less than 100 seconds after the 1st gush, and less than 300 seconds, or less than 200 seconds after the 2nd gush, and less than 500 seconds, or less than 300 seconds after the 3rd gush, as measured according to the Modified Fluid Acquisition test method set out herein.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Sanitary Napkin

Figure 9:
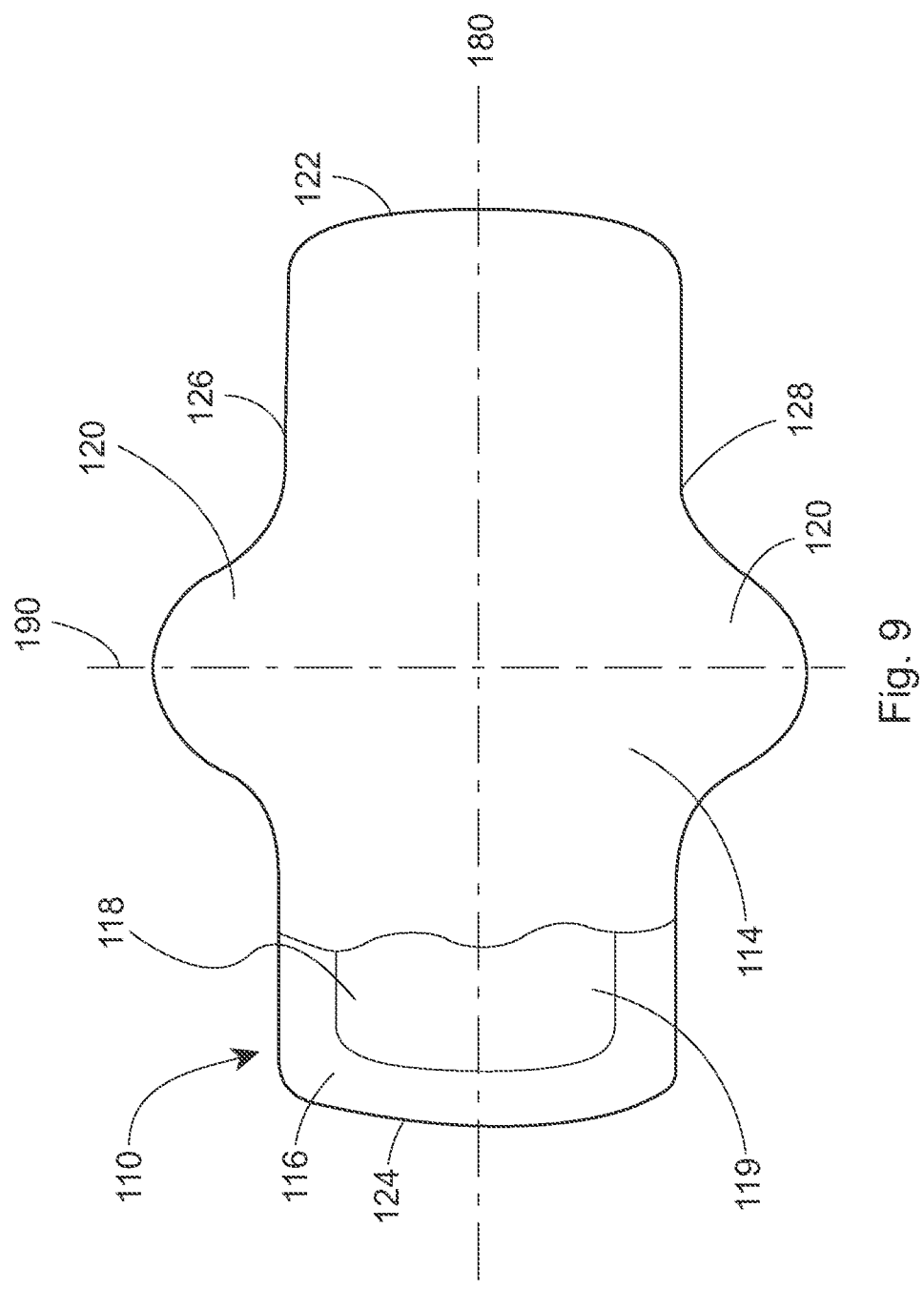
FIG. 9 is a plan view of an example absorbent article of the present disclosure that is a sanitary napkin.
Figure 10:
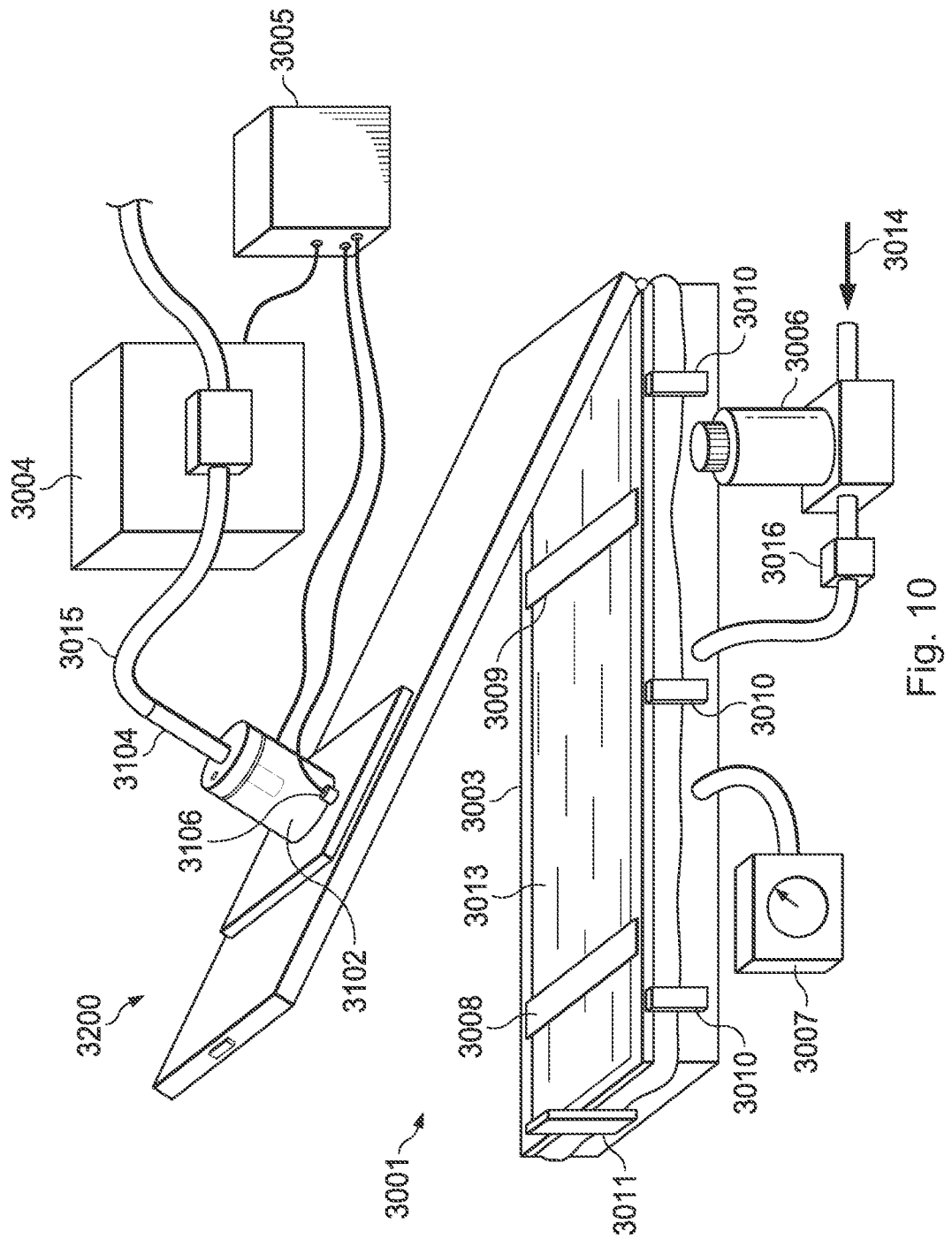
FIG. 10 illustrates an apparatus used in the Modified Fluid Acquisition Test.

Referring to FIG. 9, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Bio-Based Content for Components

Components of the absorbent articles described herein may at least partially be comprised of bio-based content as described in U.S. Pat. Appl. No. 2007/0219521A1. For example, the superabsorbent polymer component may be or may be partially bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S.A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Pat. Appl. Publ. No. 2019/0192723, published on Jun. 27, 2019.

Test Methods

Unless otherwise indicated in the test method, all measurements are performed at a temperature of 23° C. (±2° C.) and a relative humidity of 45% (+/−10%), unless specified otherwise. All samples are kept at least 24 hours in these conditions to equilibrate before conducting the tests, unless indicated otherwise. All measurements are reproduced on at least 4 samples and the average value obtained indicated, unless otherwise indicated.

Amount of Extractables Test Method

This test method is used to quantify the mass fraction of soluble polymers of SAF that is extracted into physiological saline solution (0.9 weight-% NaCl in deionized water) via gravimetric analysis (hereinafter referred to as "amount of extractables"). The amount of extractables is determined via the dry weight of soluble components such as soluble polymers, oligomers and/or monomers in the extraction liquid.

Equipment:

Analytical Balance, Mettler Toledo AX 205 DR/XP 1203 S

Erlenmeyer Flask 250 mL, VWR 214-1172

Tweezers

Parafilm, FILM SEALING PARAFILM® L75M W. 100 MM 1, VWR 291-1212

Circular Shaker, IKA KS 501 D equipped with universal attachment AS 501.1

Buechner Funnel (porcelain, Ø110 mm), VWR 511-2507

Filtering Flask (1-armed, 1000 mL equipped with neck-sealing), VWR SART16606

Filter Papers (Ø110 mm), Whatman 597, VWR 515-4309

Filtration cylinder:

made of transparent polycarbonate (e.g., Lexan®) and has an inner diameter of 6.00 cm (area=28.27 cm$^2$) with inner cylinder walls which are smooth. The bottom of the cylinder is faced with a stainless-steel screen cloth (ISO 9044 Material 1.4401, mesh size 0.038 mm, wire diameter 0.025 mm) that is bi-axially stretched to tautness prior to attachment to the bottom of the cylinder. The height of the filtration cylinder is approximately 60.5 mm.

Water Jet Pump Buerkle, BURK9668-0200

Beaker 50 mL, VWR 213-0462P 40 mL Glass Vials, 30×80 mm, VWR 548-0650

Pasteur pipettes, disposable 3 ml, VWR 612-1681

Sieve, Retsch 45 μm Ø20 cm 510-4607

Vacuum Oven, Heraeus VT 6130 P-BL

Cooling trap, Kinetics Titan Trap 8 L

Vacuum Pump, Vacuubrand PC 2004 Vario

Equipment—or part of the equipment—can be replaced by equivalent equipment.

Chemicals:

Use only reagents of recognized analytical grade, unless otherwise specified.

Deionized Water: >5 MΩ cm at 25° C. (e.g. from Millipore purification system)

Sodium Chloride ≥99.0% purity (e.g. from Merck, 1.06400.1000)

Preparation of Sodium Chloride Solution (0.9 Weight-%):

The accuracy of the concentration of the sodium chloride solution is important for the accuracy of the test result, as sodium chloride salt remains in the dried residuals and is subtracted (see equation 1), so the Amount of Extractables is the mass fraction of the extractable components of the superabsorbent fibers or of the nonwoven(s) comprising the superabsorbent fibers.

Procedure of Preparation of 0.9 Weight-% Saline Solution:

A clean volumetric flask with the appropriate volume (minimum volume of 1.0 L) (accuracy of at least 0.10%) for the preparation of 0.9 weight-% saline solution is filled to half of its final volume with deionized water and equipped with a clean stirring bar of suitable size. The volumetric flask is placed on a magnetic stirrer and a suitable rotation speed is chosen. The speed is suitable when a clear vortex develops in the solution and thus an adequate mixing is ensured. The required amount of sodium chloride for the preparation of 0.9 weight-% saline solution is weighed to accuracy of at least 0.11% of the amount of sodium chloride into a clean and dry weighing container (e.g. beaker) of appropriate size. The sodium chloride is added into the volumetric flask. The solution is stirred until the sodium chloride has totally dissolved. Total dissolution is achieved when no solid chemical is observed remaining in the solution.

The weighing container (e.g. beaker) that contained the sodium chloride is cleaned with deionized water which is then directly added into the flask to ensure the complete carryover of all sodium chloride. The neck of the volumetric flask is cleaned at its inner side with deionized water before filling the volumetric flask to the final volume to ensure the complete carryover of all sodium chloride into the solution. The solution is stirred well to ensure all the sodium chloride has totally dissolved. Before filling up to final volume the stirring bar is removed from the flask using a magnetic rod. The stir bar and rod are rinsed with deionized water directly into the flask to ensure the complete carryover of all material. The volumetric flask is filled with deionized water to the appropriate volume (accuracy of at least 0.10%) for the preparation of 0.9 weight-% saline solution. (In volumetric flasks, typically the defined volume of the flask is reached if the lower meniscus of the solution just touches the upper edge of the calibration line. After filling up to the final volume, the final solution is mixed well (e.g. shaken and/or stirred) in order to achieve uniform distribution of all components of the solution (to avoid any concentration gradient in the 0.9 weight-% saline solution).

Sample Preparation for Amount of Extractables:

Samples are stored in closed containers or bags, e.g. Ziplock bags, to prevent absorption of atmospheric moisture, and allowed to equilibrate to the laboratory conditions for at least 24 hours.

The superabsorbent fibers and/or nonwoven web(s) comprising superabsorbent fibers are cut into pieces with approximately 5 mm as largest dimension. The cutting can e.g. be done manually with scissors. Care is taken that the fibrous structure (i.e. the nonwoven web or the bulk of fibers) is not majorly compressed before or during the cutting process. This ensures sufficient void space between the superabsorbent fibers or in the nonwoven web(s), respectively, so they can be predominately wetted by the extraction medium at the entire surface area.

Procedure of Amount of Extractables:

1.00 g (±0.05 g) of the fibrous structure sample (superabsorbent fibers or in the nonwoven web(s) comprising superabsorbent fibers) is weighed into a 250 mL Erlenmeyer flask. The mass $m_1$ of the fibrous structure sample is recorded to nearest 0.001 g. 200 g (±1 g) of 0.9 weight-% saline (prepared as described above) is added to the 250 mL Erlenmeyer flask with the fibrous structure sample. The mass of the saline is recorded as $m_s$ to nearest 0.001 g. The Erlenmeyer flask is closed with parafilm (e.g. FILM SEAL-ING PARAFILM® L75M W. 100 MM 1, VWR 291-1212), placed onto a circular shaker (e.g. IKA KS 501 D equipped with universal attachment AS 501.1) and fixed with the universal attachment. The Erlenmeyer flask is shaken by the circular shaker at 150 rpm for 16 hours.

The filtering flask is equipped with a neck sealing and a Buechner funnel (e.g. porcelain funnel, Ø110 mm, VWR 511-2507) and connected to a vacuum ejector (e.g. Water Jet Pump Buerkle, BURK9668-0200). A filter paper (e.g. Filter Papers (Ø110 mm), Whatman 597, VWR 515-4309) is placed flat into the Buechner funnel. The filtration cylinder is placed on top of the filter paper, in the central position of the Buechner funnel, such that the filter paper underneath remains flat and without wrinkles or folds. Then, the filtering flask is evacuated by starting the vacuum ejector. The Erlenmeyer flask is taken from the circular shaker and the filter paper is carefully wetted with few milliliters of the extraction solution via a Pasteur pipette to ensure all perforations in the funnel are closely covered by the filter paper. The remaining extraction mixture in the Erlenmeyer flask is then added to the filtration cylinder on the Buchner funnel such that the filtration cylinder is not filled completely, i.e. up to its upper opening, at any time. After the complete extraction mixture from the Erlenmeyer flask is added to the filtration cylinder, filtration via the vacuum ejector is continued for at least approx. 2 minutes or, if filtration is not completed after 2 minutes, until no more liquid is flowing or dropping through the funnel. Afterwards, the vacuum ejector is stopped and the Buechner funnel with the filter paper and the filtration cylinder is removed from the filtration flask. A dry and clean glass vial (e.g. 40 mL Glass Vials, 30×80 mm, VWR 548-0650) is weighed and the mass is recorded as $m_v$ to nearest 0.0001 g. 3 g (±0.0500 g) of the filtrate (filtered extraction solution in the filtration flask) recorded as mass $m_1$ to nearest 0.0001 g, is added into the glass vial. The glass vial is covered with a screen (e.g. Sieve, Retsch 45 µm Ø20 cm 510-4607) to avoid any loss of solid or solution during drying.

The filtrate in the glass vial covered with the screen is dried in a vacuum oven at 40° C. at <10 mbar for at least 24 hours. The drying is continued till the sample is fully dried (till the mass remains constant), but not longer than 96 hours.

After drying, the sample is weighed in the glass vial and the mass $m_4$ is recorded to nearest 0.0001 g, giving the dry weight of glass vial with dried extract (i.e. the residual of the liquid phase). In case any solid is attached to the screen, it is transferred into the vial before the mass $m_4$ is determined. Alternatively, the mass of the screen before and after drying is determined and the difference is added to the mass of the vial with the dried extract to give $m_4$. Note: In case the difference in screen weight before and after drying is negative, it is considered to be 0 (zero).

For each superabsorbent fiber sample or nonwoven web (s) sample comprising superabsorbent fibers, typically 4 extractions are done. For each extraction, at least 2 dryings are done. This results in typically 8 glass vials with dried extract, called herein 8 "replicates". The amount of extractables is determined based on at least 4 replicates, typically based on 8 replicates.

Calculation:

Amount of extractables (weight-%) via Extraction Liquid
a. Extracted Amount of solid (g)=$m_e$ $$m_e = m_4 - m_v - 0.009 \cdot m_l \tag{1}$$

b. Extractables=extr.

$$extr. = \frac{m_s \cdot m_e}{(m_l - m_e) \cdot m_1} \tag{2}$$

The mean of all replicates of "extr." is calculated and given as "amount of extractables" in weight-%.

In case a replicate shows a negative value for "extr." (this can occur for very small amount of extractables as the dry sodium chloride amount is subtracted from the dried solid (see equation 1), this replicate is discarded. In case at least 4 replicates of the respective superabsorbent fiber sample or nonwoven web(s) sample comprising superabsorbent fibers show positive values for "extr.", the average of these replicates is taken to give amount of extractables" in weight-%.

In case less than 4 replicates (out of the 8 replicates done) of the respective superabsorbent fiber sample or nonwoven web(s) sample comprising superabsorbent fibers show positive values for "extr.", "amount of extractable" for that sample is defined as <10 weight-%.

Titratable Soluble Test Method

This test method is used to quantify titratable soluble after extraction of superabsorbent fiber sample or nonwoven web(s) sample comprising superabsorbent fibers with 0.9 weight-% saline.

Preparation of 0.9 weight-% saline as described under Test Method "Amount of Extractables" herein.

Sample Preparation for Titratable Soluble:

Samples are stored in closed containers or bags, e.g. Ziplock bags, to prevent absorption of atmospheric moisture, and allowed to equilibrate to the laboratory conditions for at least 24 hours.

The superabsorbent fibers and/or nonwoven web(s) comprising superabsorbent fibers are cut into pieces with approximately 5 mm as largest dimension. The cutting can e.g. be done manually with scissors. Care is taken that the fibrous structure (i.e. the nonwoven web or the bulk of fibers) is not majorly compressed before or during the cutting process. This ensures sufficient void space between the superabsorbent fibers or in the nonwoven web(s), respectively, so they can be predominately wetted by the extraction medium at the entire surface area.

Procedure of Titratable Soluble:

The test method titratable soluble is executed according to the procedure described in EDANA NWSP 270.0.R2 (19) with extraction time of 16 hours, instead of 1 hour and except the sampling (chapter 8 of EDANA NWSP 270.0.R2 (19), "Sampling"). The sample preparation for titratable soluble is done as described above.

The calculation of titratable soluble is done according to the calculation of the extractable content, w, in chapter 10 "Calculation" of EDANA NWSP 270.0.R2 (19). Titratable soluble is given in %.

Notably, titratable soluble may not represent a mass fraction, as the molecular weight of the monomeric components in the superabsorbent fibers and/or nonwoven web(s) comprising superabsorbent fibers might be different to the molecular weights used in EDANA NWSP 270.0.R2 (19) in chapter 10, $M_{COOH}$ and $M_{COONa}$.

Dry Absorbent Core Caliper Test

This test is used to measure the caliper of the absorbent core (before use i.e. without fluid loading) in a standardized manner.

Equipment: Mitutoyo manual caliper gauge with a resolution of 0.01 mm—or equivalent instrument. Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample. The caliper gauge is mounted with the lower surface of the contact foot in a horizontal plane so that the lower surface of the contact foot contacts the center of the flat horizontal upper surface of a base plate approximately 20 cm×25 cm. The gauge is set to read zero with the contact foot resting on the base plate.

Ruler: Calibrated metal ruler graduated in mm.
Stopwatch: Accuracy 1 second

Sample preparation: The core is conditioned at least 24 hours as indicated above.

If the absorbent core has to be removed from an absorbent article, such as a diaper, all other components of the absorbent article are carefully removed, paying attention not to damage the absorbent core. If needed, surfactant-free ice spray can be used to facilitate removal of the absorbent core.

Measurement procedure: The core is laid flat with the bottom side, i.e. the side intended to be placed towards the backsheet in the finished article facing down. The point of measurement is carefully drawn on the top side of the core taking care not to compress or deform the core. The contact foot of the caliper gauge is raised and the core is placed flat on the base plate of the caliper gauge with the top side of the core up so that when lowered, the center of the foot is on the marked measuring point. The foot is gently lowered onto the article and released (ensure calibration to "0" prior to the start of the measurement). The caliper value is read to the nearest 0.01 mm, 10 seconds after the foot is released.
Determination of Basis Weight Basis weight of a nonwoven web or of more than one nonwoven web on top of each other or of an absorbent core may be determined using NWSP 130.1 RO(15) (EDANA). The corresponding normative reference is ISO 12625-6: 2016; Tissue paper and tissue products—Part 6: Determination of grammage.
Porosity Test Method Porosity can be calculated from basis weight, caliper, and specific fiber density.

Porosity can be calculated with:

$$n = 1 - \frac{BW}{d \cdot \rho_{fib}}$$

wherein
$r_{fib}$ is the density of the fibers
d is the caliper of the nonwoven web
BW is the basis weight of the nonwoven web
n is the porosity
The density $r_{fib}$ of the fibers can be determined by pycnometry with a suitable non-swelling liquid of known density.

The caliper (d) is measured with the dry absorbent core caliper test method above.

Basis weight (BW) is determined by the above test method for determining basis weight.
Modified Fluid Acquisition Test The Modified Fluid Acquisition ("MFA") Test is designed to measure the speed at which 0.9 weight-% saline solution is absorbed into an absorbent core that is compressed at 2.07 kPa. Additional layers may be placed on top and/or below the absorbent core for the Modified Fluid Acquisition Test (see Examples below), in which case the MFA determines the speed at which 0.9 weight-% saline solution is absorbed into an absorbent core and the additional layers that is compressed at 2.07 kPa.

A known volume is introduced four times, each successive dose starting five (5) minutes after the previous dose has absorbed. Times needed to absorb each dose are recorded. The test fluid is 0.9 weight-% w/v saline solution and is prepared by weighing 9.0 g±0.05 g of NaCl into a weigh boat, transferring it into a 1 L volumetric flask, and diluting to volume with de-ionized water.

The MFA apparatus is depicted in FIG. 10 through FIG. 12B. The MFA apparatus comprises a bladder assembly 3001 and a top plate assembly 3200 that includes a deposition assembly 3100. A controller 3005 is used to 1) monitor the impedance across electrodes 3106, recording the time interval 0.9 weight-% saline solution is in a cylinder 3102, 2) interface with a liquid pump 3004 to start/stop dispensing, and 3) time intervals between dosing. The controller 3005 is capable of recording time events to ±0.01 sec. A house air supply 3014 is connected to a pressure regulator 3006 capable of delivering air at a suitable flow/pressure to maintain 2.07 kPa in the bladder assembly 3001. A liquid pump 3004 (Ismatec MCP-Z gear pump, available from Cole Palmer, Vernon Hills, Ill. or equivalent) capable of delivering a flow of 10-80 mL at a rate of 3-15 mL/s is attached to a stainless steel tube 3104 of the deposition assembly 3100 via tygon tubing 3015.

The bladder assembly 3001 is constructed of 12.7 mm Plexiglas with an overall dimension of 80 cm long by 30 cm wide by 10 cm tall. A manometer 3007 to measure the pressure inside the assembly and a pressure gauge 3006 to regulate the introduction of air into the assembly are installed through two holes through the light side. A bladder 3013 is assembled by draping a 50 mm by 100 mm piece of silicone film, (thickness 0.02", Shore A durometer value of 20, available as Part #86435K85 from McMaster-Carr, Cleveland, Ohio) over the top of the box with enough slack that the film touches the bottom of the box at its center point. An aluminum frame 3003 with a flange is fitted over the top of the film and secured in place using mechanical clamps 3010.

When in place, the assembly should be leak free at a pressure of 3.45 kPa. A front 3008 and back 3009 sample support of 5 cm by 30 cm by 1 mm are used to anchor the sample. The absorbent core (optionally with additional layers on top and/or below) is attached to the top surface of the sample supports by either adhesive tape or mechanical "hook" fasteners. These supports can be adjusted along the length of the aluminum frame 3003 via a simple pin and hole system to accommodate different size absorbent cores and to correctly align their loading point.

Figure 12B:
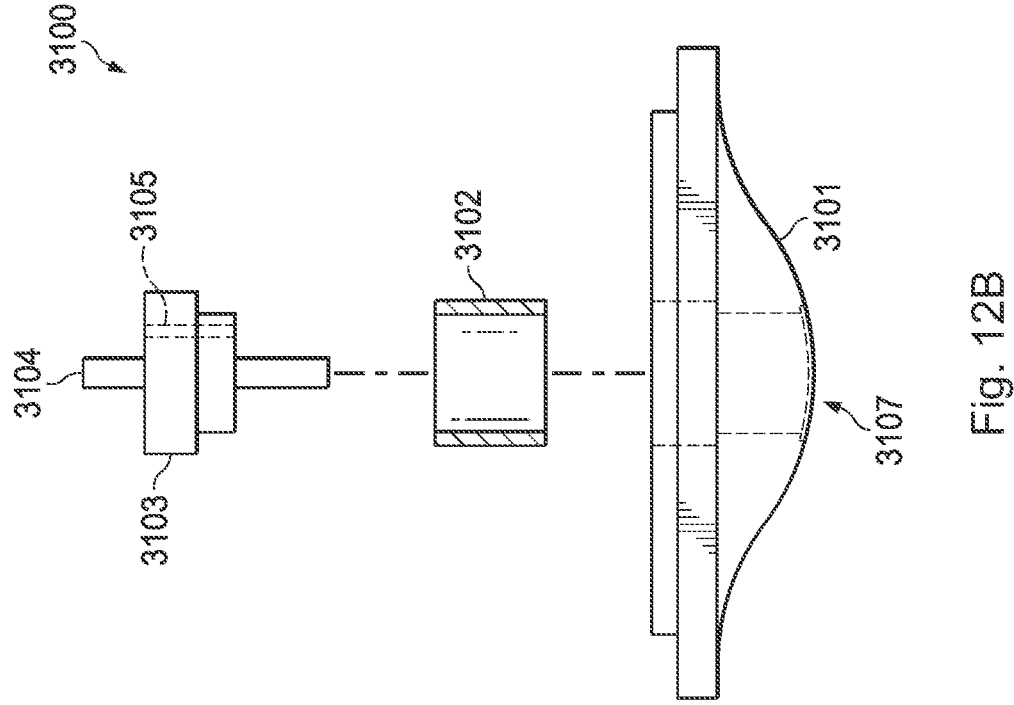
FIG. 12B illustrates equipment used in the Modified Fluid Acquisition Test.
Figure 12A:
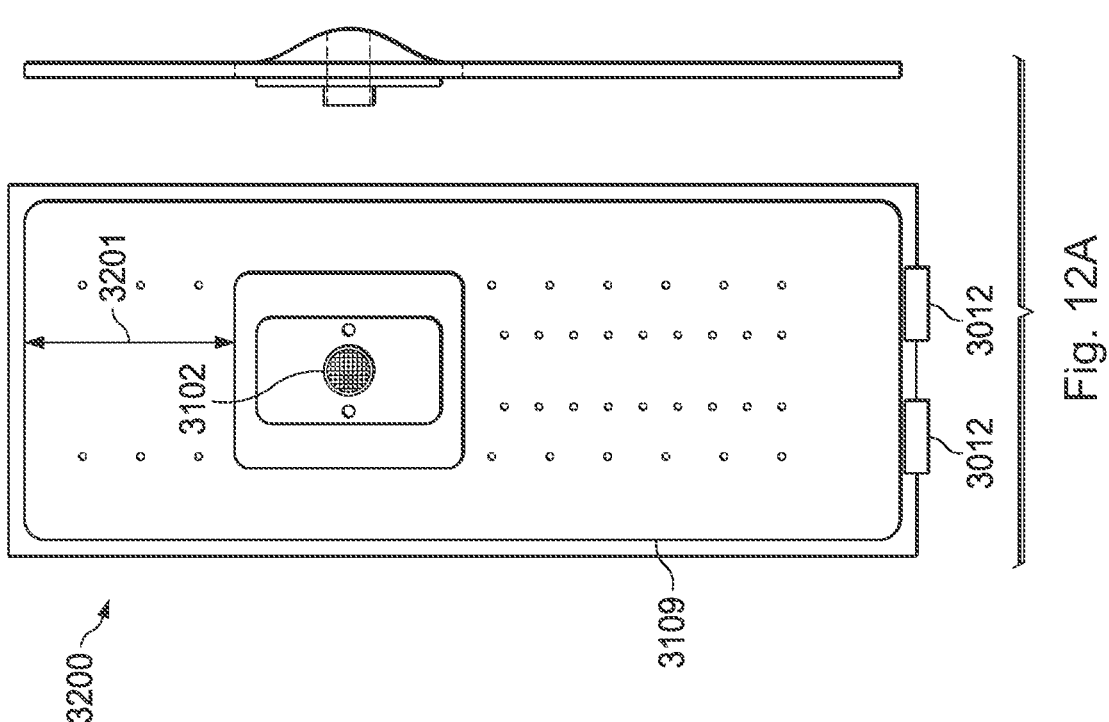
FIG. 12A illustrates a top plate assembly used in the Modified Fluid Acquisition Test.

The top plate assembly 3200 is constructed of an 80 cm by 30 cm piece of 12.7 mm Plexiglas reinforced with an aluminum frame 3109 to enhance rigidity. The plate has a cutout 170 mm wide by 201 mm long centered laterally on the plate, 170 mm from the front of the plate 3201 for mounting of the deposition assembly. In addition, the top plate has thirty-six (36) 3.2 mm diameter holes drilled through it distributed as shown in FIG. 12A. The holes prevent air from being trapped under the top plate as the bladder is inflated. The top plate assembly 3200 is connected to the bladder assembly 3001 via two hinges 3012. During use, the top assembly is closed onto the bladder assembly and locked into place using a mechanical clamp 3011.

Figure 11A:
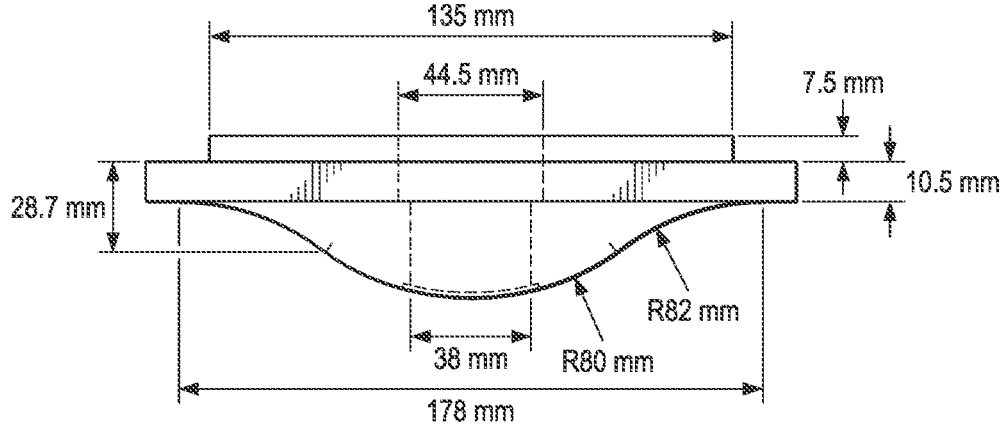
FIG. 11A is a side view of the curved component used in the Modified Fluid Acquisition Test.
Figure 11B:
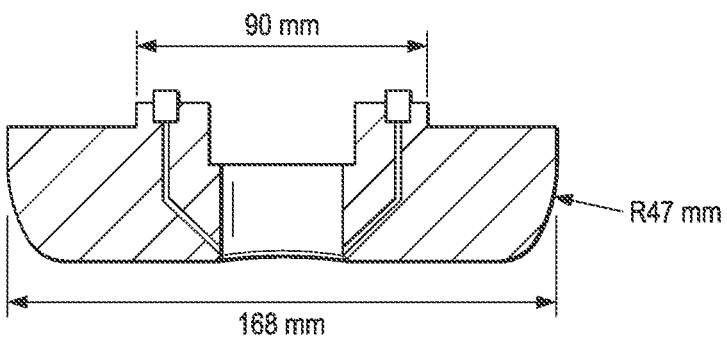
FIG. 11B is an end view of the curved component of FIG. 11A.
Figure 11C:
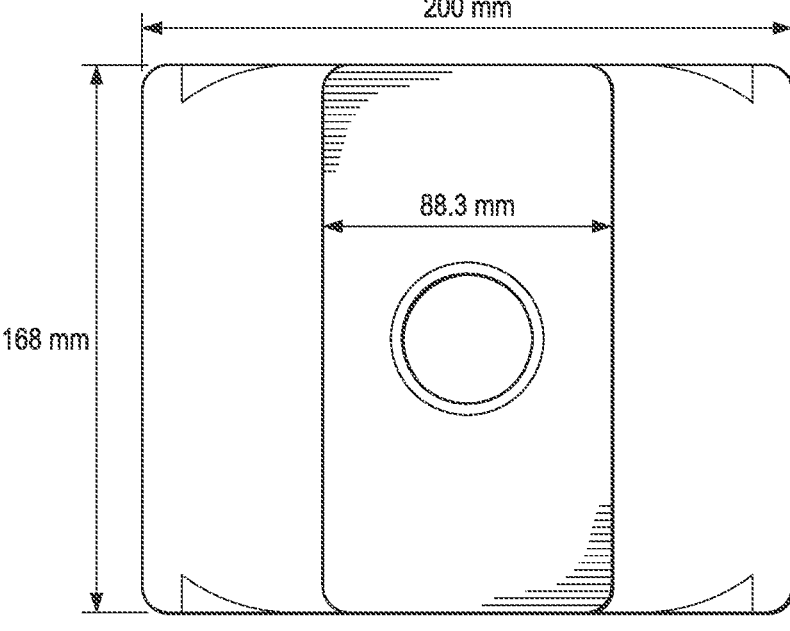
FIG. 11C is a bottom view of the curved component of FIG. 11A.
Figure 11D:
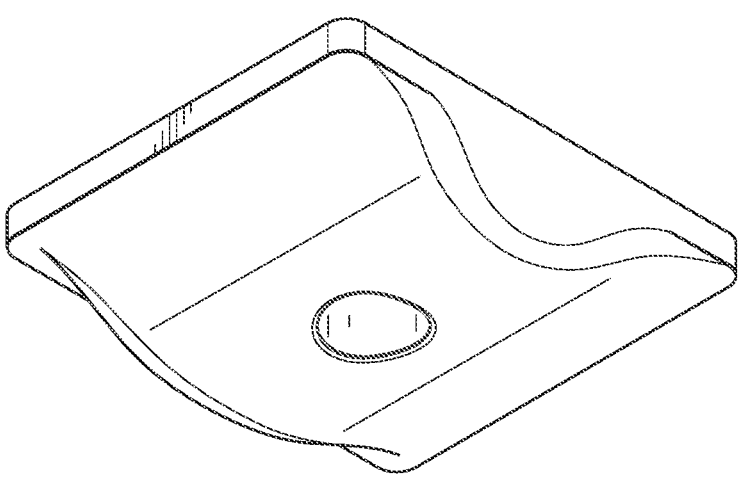
FIG. 11D is a bottom perspective view of the curved component of FIG. 11A.
Figure 11E:
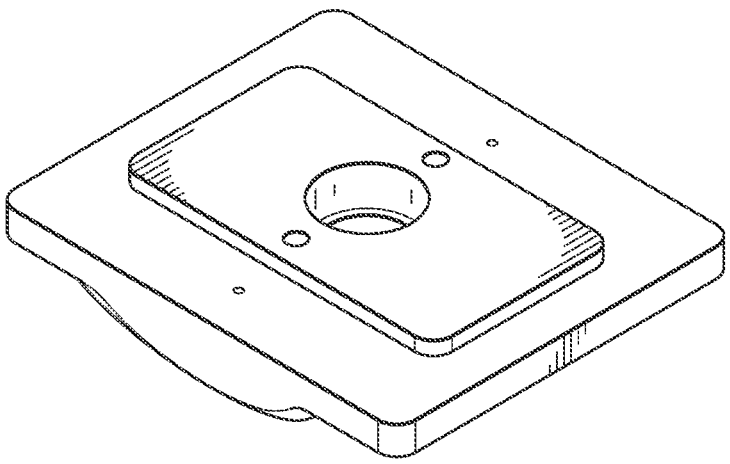
FIG. 11E is a top perspective view of the curved component of FIG. 11A.

The deposition assembly 3100 is fitted into the top plate 3200 and includes 1) a liquid introduction cylinder 3102, 2) a curved surface 3101 at the loading point of the absorbent core and 3) electrodes 3106 that are used to detect fluid in the cylinder 3102. The detailed dimensions of the curved component are provided in FIG. 11A to FIG. 11E. FIG. 11A is a side view of the curved component. FIG. 11B is an end view of the curved component. FIG. 11C is a bottom view of the curved component. FIG. 11D is a bottom perspective view of the curved component. FIG. 11E is a top perspective view of the curved component. This curved component can be milled or 3D printed. The top portion of the introduction cylinder is a 50.8 mm O.D. Plexiglas cylinder 3102 with a 38.1 mm I.D. This is fitted into the curved component to give the introduction cylinder a total height of 100 mm. Imbedded electrodes run from connectors on the upper surface of the curved component and terminate flush with an inside wall of the introduction cylinder, 2 mm from the bottom of the cylinder. The two electrodes are positioned 180 degrees apart. A nylon screen 3107 is cut and affixed flush with the bottom of the cylinder such that the sample cannot swell into the cylinder. A 5 mm semi-circle is cut in the screen in the immediate area of the two electrodes. The deposition assembly is inserted into the top plate as shown in FIG. 12A such that the curved surface is flush with the bottom of the top-plate assembly 3200. The introduction cylinder 3102 is topped with a loose-fitting nylon cap 3103. The cap has a 6.35 mm O.D. steel tube 3104 inserted through its center. When the cap is in place, the bottom of the tube ends 20 mm above the screen 3107. The cap also has an air hole 3105 to ensure negative pressure does not impede the absorption speed.

Place the absorbent core flat onto a lab bench and identify the intersection of the longitudinal centerline with the loading point as defined in Table 1.

Conditions for Modified Fluid Acquisition Testing:

| Loading Point from front of Core mm | Gush Volume mL | Flow Rate mL/s | Delivery Time s | Number of subsequent gushes |
|---|---|---|---|---|
| 170 | 75 | 15 | 5 | 4 |

Attach the end of the absorbent core, which is intended to be placed towards the front end of the absorbent article (i.e. the front waist region for a diaper or pant), to the top surface of the front sample plate 3008 by either adhesive tape or mechanical "hook" fasteners with a topsheet facing upward. For absorbent cores which are symmetric along their transverse axis, it is not relevant which end of the absorbent core is attached to the top surface of the front sample plate 3008. The placement is such that no parts of the absorbent core overlay the plate. The sample plate 3008 is attached to the aluminum frame 3003 such that the size-dependent (i.e. size of the absorbent article into which the absorbent core is intended to be provided) Loading Point (as defined in the Table above) of the absorbent core will be centered longitudinally and laterally within the cylinder 3102 when the top plate assembly has been closed. The end of the absorbent core, which is intended to be placed towards the back end of the absorbent article, is secured to the back sample plate 3009 by either adhesive tape or mechanical "hook" fasteners, once again ensuring that no parts of the absorbent core overlay the plate. The back sample plate 3009 is then attached to the aluminum frame 3003 such that the absorbent core is taunt but not stretched. The top plate assembly is closed and fastened, and the bladder is inflated to 2.07 kPa±0.07 kPa. The pressure is maintained at this level during the complete loading sequence of the test.

The pump 3004 is primed and then calibrated to deliver the size-dependent volume and flow rate selected from Table 1. Volume and flow rate must be within ±2% of target. The cap 3103 is placed into the cylinder 3102. The controller 3005 is started, which in turn delivers the first dose of 0.9 weight-% saline solution. After the volume has been absorbed, the controller waits for 5.0 minutes before addition of the next dose. This cycle is repeated for a total of four doses. If the fluid leaks out of or around the article (i.e., is not absorbed into the article) then the test is aborted. Also, if any acquisition time exceeds 1200 seconds, the test is aborted. The acquisition time is defined as the difference between the start time (i.e., when the 0.9 weight-% saline is first introduced into the cylinder and that conducting fluid completes the circuit between the electrodes) and the stop time (i.e., when the fluid has completely drained from the cylinder and the circuit between the electrodes is broken). Acquisition times are recorded by the controller for each dose to the nearest 1.0 second. After the last dose is acquired, pressure is applied for an additional 10 minutes. Open the pressure relief valve 3016 to deflate the bladder and then remove the sample from the acquisition system.

In the same fashion, run a total of four (4) replicates for each absorbent core to be evaluated. Calculate and report the Acquisition Times (sec) for each dose as the arithmetic mean of the replicates to the nearest 1.0 sec.

As said above, additional layers may be placed on top of the absorbent core, prior to testing, such as topsheet materials and/or layers that are used as acquisition materials in an absorbent article. Also, a liquid impervious polyolefin film may be provided underneath the absorbent core, i.e. between the absorbent core and the sample plate. Such additional layers, if applied in the Examples, are described in more detail in the Examples below.

Centrifuge Retention Capacity (CRC) Test Method

Capacity of the superabsorbent fibers, the capacity of the nonwoven web(s) with superabsorbent fibers and the capacity of the absorbent core is determined according to the Centrifuge Retention Capacity (CRC) test method as set out in EDANA NWSP 241.0.R2(19). In deviation from EDANA NWSP 241.0.R2(19) the sampling (chapter 8 in EDANA NWSP 241.0.R2(19)) for the superabsorbent fibers, nonwoven web(s) with superabsorbent fibers and/or the absorbent core is as following:

The superabsorbent fibers, nonwoven web(s) with superabsorbent fibers and/or the absorbent core are cut into pieces with approximately 5 mm as largest dimension. The cutting can e.g. be done manually with scissors. Care is taken that the fibrous structure (the core, the nonwoven or the bulk of fibers) is not majorly compressed before or during the cutting process. This ensures sufficient void space between the superabsorbent fibers, so they can be predominately wetted by the swelling medium at the entire surface area.

Further deviations from or additions to EDANA NWSP 241.0.R2(19) in the procedure (chapter 9.1-9.5 in EDANA NWSP 241.0.R2(19)) for the superabsorbent fibers, nonwoven web(s) with superabsorbent fibers and/or the absorbent core are as following:

The sample for the measurement is taken carefully, e.g. with a lab tweezer, to put it into the teabag. With a lab tweezer, the fibers are carefully distributed in the teabag to avoid lumps and fiber lumps, if any, are carefully opened.

When sealing the teabag, care is taken that no material of the superabsorbent fibers, nonwoven web(s) with superabsorbent fibers and/or the absorbent core is in the area of the seal. This ensures a complete and sufficiently strong sealing of the teabag.

All other items of the test method are executed as set out in EDANA NWSP 241.0.R2(19).

EXAMPLES a) Examples 1-4 with Various Surfactants

In Examples 1 to 4, needle-punched (also referred to as "needlefelt") nonwoven webs made of staple superabsorbent the nonwoven web material as commercially available from Technical Absorbents Ltd. as Product Type 7125 was used "as is" to prepare the absorbent core.

The prepared absorbent core samples were equilibrated for 24 h at a temperature of 21° C. (±2° C.) and a relative humidity of 50% (+/−5%) prior to being subjected to the Modified Fluid Acquisition Test.

The following average acquisition times have been measured.

TABLE 1

|  | | average acquisition times | | |
|---|---|---|---|---|
| Example | Surfactant (surfactant class of the respective surfactant) | Gush 1 [s] | Gush 2 [s] | Gush 3 [s] |
| Comparative Example 1 | no surfactant (none) | 530 | 657 | >1200 |
| Example 1 | Stantex ® K 1342 available from Pulcra Chemicals | 111 | 256 | 477 |
| Example 2 | Hedipin ® CFA/100 available from Dr. W. Kolb AG, Switzerland (ethoxylated fatty acid) | 45 | 141 | 193 |
| Example 3 | Marlipal ® 24/99; Sasol Germany GmbH (ethoxylated C12-C14 alcohols) | 47 | 79 | 124 |
| Example 4 | Tergitol ® Type 15-S-7; Sigma-Aldrich Chemie (polyglycol ether, non-ionic surfactant) | 47 | 101 | 160 | fibers and available from Technical Absorbents Ltd. As Product Type 7125 were subjected to spray-coating with various different surfactants and the average acquisition times were determined according to the Modified Fluid Acquisition test method set out above.

As determined by the test methods set out above, the nonwoven webs had a basis weight of 300 g/m$^2$ a porosity of 96% capacity of 7 g/g, an amount of extractables of <10 weight-% based on the total weight of the nonwoven web, and an amount of titratable soluble of 2.5%.

The nonwoven webs were cut into rectangular samples each having a width of 170 mm and a length of 420 mm.

The sample nonwoven webs were laid down on a table and one of the outer surfaces of the nonwoven web samples were spray-coated with 0.5 weight-% of surfactant (see Table 1 for details on surfactant)

Subsequently, to obtain an absorbent core of the present invention, two of the spray-coated nonwoven web samples were placed on top of each other with their perimeters being aligned and congruent in width and length dimension such that the surfaces of the nonwoven web samples which were subjected to spray-coating are facing outwardly and the non-spray coated surfaces being in direct contact with each other. The two nonwoven web samples placed on top of each other were spray-coated with the same surfactant.

The dry weight of each absorbent core (i.e. prior to subjecting it to the Modified Fluid Acquisition test method) was 43 g.

As a comparative example (Comparative Example 1), an absorbent core was prepared as described above with without any spray-coating or other treatment with surfactant, so As is apparent from the data in Table 1, fluid acquisition times decreased very significantly for all examples vs. the Comparative Example 1, i.e. for all 4 different surfactants that were tested.

b) Examples 5-7 and Comparative Examples 2-3

For each of Examples 5-7 and for Comparative Examples 2 and 3, superabsorbent fibers commercially available from Technical Absorbents Ltd. as SAF 112/52/10 were converted into nonwoven webs. The fibers had a length of 52 mm and a diameter of 10 dtex.

The nonwoven web had a capacity of 26.7 g/g, an amount of extractables of 21.2 weight-% based on the total weight of the nonwoven web, and an amount of titratable soluble of 27.0%. The capacity and amount of extractable and amount of titratable soluble changed for Examples 5-7 upon heat treatment, see below.

Conversion of the fibers into nonwoven webs was done by needle-punching. The basis weight of the nonwoven web obtained after conversion was 300 g/m$^2$, the porosity was 96%.

The nonwoven webs were cut into rectangular samples each having a width of 110 mm and a length of 360 mm.

The sample nonwoven webs were laid down on a table and both of the outer surfaces of the nonwoven web samples were spray-coated with 0.5 weight-% of surfactant Hedipin® CFA/100 available from Dr. W. Kolb AG, Switzerland. These nonwoven webs treated with the surfactant were used in Examples 5-7 and Comparative Examples 2 and 3.

The absorbent core and test specimen for Examples 5-7 and Comparative Examples 2 and 4 were as follows:

Comparative Example 2: For Comparative Example 2, two of the sample nonwoven webs, cut to a size of 110×360 mm and treated with surfactant as described above, were placed on top of each other with their perimeters being aligned and congruent in width and length dimension to obtain the absorbent core of Comparative Example 2.

Example 5: For Example 5, two nonwoven webs, cut to a size of 110×360 mm and treated with surfactant as described above, were placed in a pre-heated oven at 220° C. for 5 minutes. The capacity and amount of extractables was of superabsorbent fibers derived from the nonwoven webs was measured (according to the test methods set out above after the nonwoven webs were taken out of the oven. The capacity was determined as 13.5 g/g and the amount of extractables was determined as <10 weight-% and the amount of titratable soluble was determined as 5.1%.

Hence, subjecting the nonwoven webs to heating significantly reduced the amount of extractables. At the same time, the capacity was also decreased, however, to an extent that the capacity after heat treatment still provides superabsorbent fibers suitable for use in the absorbent cores of the present invention.

After the heat treatment, two of the sample nonwoven webs were placed on top of each other with their perimeters being aligned and congruent in width and length dimension to obtain the absorbent core of Example 5.

Comparative Example 3: For Comparative Example 3, the same absorbent core as used in Comparative Example 2 was applied. An acquisition material made of a resin bonded nonwoven web of 70 weight-% PET fibers and 30% latex binder was laid on top of the absorbent core.

The acquisition material used in Comparative Example 3 is commercially available in Pampers Baby Dry diaper as sold in Germany in 2020. In the commercial Pampers Baby Dry diapers, the material is provided directly underneath the topsheet.

The layer of acquisition material in Comparative Example 3 had a width of 90 mm and a length of 360 mm. It was placed on top of the absorbent core with transverse edges being aligned and congruent with the transverse edges of the absorbent core and such that the acquisition material was centered in the width direction, i.e. the longitudinal edges of the acquisition material were 10 mm inboard of the longitudinal edges of the absorbent core on both sides.

Example 6: For Example 6, the same absorbent core as used in Example 5 was used (i.e. the absorbent core wherein the nonwoven webs were subjected to a heat treatment at 220° C. for 5 min). An acquisition material made of a resin bonded nonwoven web of 70 weight-% PET fibers and 30% latex binder was laid on top of the absorbent core (the same acquisition material that that was uses in Comparative Example 3).

The layer of acquisition material in Example 6 had a width of 90 mm and a length of 360 mm. It was placed on top of the absorbent core with transverse edges being aligned and congruent with the transverse edges of the absorbent core and such that the acquisition material was centered in the width direction, i.e. the longitudinal edges of the acquisition material were 10 mm inboard of the longitudinal edges of the absorbent core on both sides.

Example 7: For Example 7, two nonwoven webs, cut to a size of 110×360 mm and treated with surfactant as described above, were placed in a pre-heated oven at 220° C. for 5 minutes. The capacity and amount of extractables was of superabsorbent fibers derived from the nonwoven webs was measured (according to the test methods set out above after the nonwoven webs were taken out of the oven. The capacity was determined as 13.5 g/g and the amount of extractables was determined as <10 weight-% and the amount of titratable soluble was determined 5.1%. After the heat treatment, two each of the two nonwoven webs were cut into the following pieces:

Two pieces of 360 mm length and 30 mm width
   One piece of 360 mm length and 50 mm width
   Each of the two pieces of 360 mm length and 30 mm width were subsequently cut into one piece of 180 mm length and 30 mm width and one piece of 170 mm length and 30 mm width (a strip of 10 mm×30 mm was thus removed).

The piece of 360 mm length and 50 mm width was subsequently cut into one piece of 180 mm length and 30 mm width and one piece of 170 mm length and 30 mm width (a strip of 10 mm×50 mm was thus removed).

The pieces of each nonwoven were arranged as follows:

The three pieces having a length of 170 mm were arranged to the front of the absorbent core, and the three pieces having a length of 180 mm were arranged to the back of the absorbent core. The pieces with a width of 50 mm being provided in the center with one piece of 30 mm width on each side. A gap (i.e. a channel) of 10 mm width was left between all pieces. The resulting absorbent core thus has a total length of 360 mm and a width of 130 mm as determined along the outer perimeter of the arranged pieces.

Each of the two nonwoven webs cut and arranged as described were placed on top of each other with their perimeters being aligned and congruent in width and length dimension and with each of the pieces in the respective nonwoven webs being placed on top of each other with their perimeters being aligned and congruent in width and length dimension. Thereby, the absorbent core of Example 7 was obtained.

An acquisition material made of a resin bonded nonwoven web of 70 weight-% PET fibers and 30% latex binder was laid on top of the absorbent core (the same acquisition material that that was uses in Comparative Examples 3 and Example 6).

The layer of acquisition material in Example 7 had a width of 90 mm and a length of 360 mm. It was placed on top of the absorbent core with transverse edges being aligned and congruent with the transverse edges of the absorbent core and such that the acquisition material was centered in the width direction, i.e. the longitudinal edges of the acquisition material were 20 mm inboard of the longitudinal edges of the absorbent core on both sides.

Following the heat treatment of the nonwoven webs with superabsorbent fibers in Examples 5-7, the nonwoven webs had the following capacity, amount of extractable and amount of titratable soluble:

Capacity (CRC) of 13.5 g/g,
   Amount of extractables of <10 weight-% based on the total weight of the nonwoven web; and
   Amount of titratable soluble of 5.1%.

For Examples 6 and 7 and Comparative Example 3, a topsheet material was placed on top of the acquisition material; in Example 5 and Comparative Example 2, where no acquisition material was used, the topsheet material was placed on top of the absorbent core. The topsheet material was a nonwoven web made of spunbond polypropylene fibers and basis weight of 12 g/m². The topsheet material was commercially available in Pampers Baby Dry diaper as sold in Germany in 2020. The topsheet material was cut to the dimensions of the absorbent core of the respective Example and placed such that the perimeters of the topsheet were aligned and congruent with the perimeters of the absorbent core.

For Examples 5-7 and Comparative Examples 1 and 2, a liquid impermeable polyolefin film was placed underneath the absorbent core and the absorbent core was adhesively attached to the polyolefin film with 5 g/m² of adhesive applied in spirals. The polyolefin film was used as backsheet film in commercially available in Pampers Baby Dry diapers as sold in Germany in 2020. Basically, any other imperme- able backsheet film used in disposable diapers would be similarly suitable.

The test specimen (including topsheet, absorbent core and polyolefin film in Comparative Example 2 and in Example 5, and including topsheet, acquisition material, absorbent core and polyolefin film in Comparative Example 3 and in Examples 6 and 7) were "closed" with ¼ inch double sided 3M tape along their perimeter.

The prepared absorbent core samples were equilibrated for 24 h at a temperature of 21° C. (±2° C.) and a relative humidity of 50% (+/−5%) prior to being subjected to the Modified Fluid Acquisition Test.

Four replicates were prepared and measured for each of Examples 5-7 and Comparative Examples 2-3. The values given in Table 2 are average values of the four replicates.

TABLE 2

Acquisition Times for Examples 5-7 and Comparative Examples 1 and 2

| Example/Comparative | average acquistion times | | | |
| --- | --- | --- | --- | --- |
| Example | Gush 1 [s] | Gush 2 [s] | Gush 3 [s] | Gush 4 [s] |
| Comparative Example 2 | >1200 | >1200 | >1200 | >1200 |
| Example 5 | 970 | >1200 | >1200 | >1200 |
| Comparative Example 3 | 157 | 337 | 457 | 556 |
| Example 6 | 65 | 155 | 208 | 316 |
| Example 7 | 26 | 109 | 189 | 277 |

Examples 1-7 as well as the Comparative Examples 1-3 were provided without any adhesive or other attachment between the nonwoven webs comprised by the absorbent core. Also, no adhesive or other attachment was used between the absorbent core and the acquisition material in Examples 6 and 7 and Comparative Example 3. Similar, no adhesive or other attachment was used between the topsheet and the acquisition material (Examples 6 and 7 and Comparative Example 3) or between topsheet and absorbent core (Example 5 and Comparative Example 2).

The acquisition times of Comparative Example 2 vs. Example 5, as well as of Comparative Example 3 vs. Example 6, show that reduction of amount of extractables and reduction of amount of titratable soluble significantly improves the acquisition performance of the samples. Nota- bly, this improvement does not appear to be offset by the reduction in capacity which also resulted from the heat treatment carried out in Examples 5-7. This applies to all gushes. Hence, also after having been to liquid gushes previously, the test specimen also exhibit fast acquisition for subsequent gushes.

Also, providing the test specimen with gaps (i.e. "chan- nels") shows a positive impact on the speed of liquid acquisition, as is reflected by Example 7 (vs. Example 6 with no channels).

While liquid acquisition times can be further improved by use of an acquisition material (Examples 6 and 7), it can be seen from Examples 1 to 4 that fast acquisition times can also be achieved when using nonwoven webs with super- absorbent fibers having low amount of extractables follow- ing treatment with surfactant.

The capacity and the amount of extractables of various superabsorbent fibers as well as nonwoven webs consisting of these superabsorbent fibers was determined in accordance with the test methods set out above.

TABLE 3

| Capacity (CRC) and amount of extractables | | | | | |
| --- | --- | --- | --- | --- | --- |
| Superabsorbent Fiber | Sample type | Used in | CRC [g/g] | Titratable soluble [%] | Amount of Extractables [weight-%] |
| SAF 141/6/10 from Technical Absorbents Ltd. | Loose superabsorbent fibers (staple fibers, 5.8 mm length and 9 dtex) | None | 28.7 | 24.3 | 11.4 |
| Product Type 7125 from Technical Absorbents Ltd. | 300 g/m² nonwoven web (needlefelt) | Examples 1-4 and Comparative Example 1 | 7.0 | 2.5 | <10 |
| SAF 102/52/10 from Technical Absorbents Ltd. | Loose superabsorbent fibers (staple fibers) | None | 26.7 | 21.2 | 28.2 |
| SAF 112/52/10 from Technical Absorbents Ltd. | Loose superabsorbent fibers (staple fibers) | Fibers used in SAF NW that is used in Comparative Examples 2-3 | 25.5 | 22.6 | 15.3 |
| SAF 112/52/10 from Technical Absorbents Ltd. | 300 g/m² nonwoven web (needlefelt) | Comparative Examples 2-3 | 26.7 | 27.0 | 21.2 |
| LANSEAL ® superabsorbent fibers FK5.6T51D, from Toyobo | Loose superabsorbent fibers (staple fibers) | none | 10.6 | 8.0 | <10 |
| SAF 112/52/10 from Technical Absorbents Ltd. | 300 g/m² nonwoven web (needlefelt) heat treated at 220° C. for 8 min | None | 9.6 | 3.6 | <10 |

TABLE 3-continued

| | | | | Titratable | Amount of |
| Superabsorbent | | | CRC | soluble | Extractables |
| Fiber | Sample type | Used in | [g/g] | [%] | [weight-%] |
|---|---|---|---|---|---|
| SAF 112/52/10 from Technical Absorbents Ltd. | 300 g/m² nonwoven web (needlefelt) heat treated at 220° C. for 5 min | Example 5-7 | 13.5 | 5.1 | <10 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, comprising any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core comprising one or more nonwoven webs, the one or more nonwoven webs comprising at least 80 weight-% of superabsorbent fibers based on the total weight of the nonwoven web, wherein the superabsorbent fibers comprise one or more surfactants; and wherein the absorbent core comprises at least 60 weight-% of the superabsorbent fibers based on the total weight of the absorbent core, wherein the one or more nonwoven webs have an amount of extractables of less than 20 weight-% based on the total weight of the one or more nonwoven webs according to the Extractables Test Method, and wherein the nonwoven webs have a capacity of at least 7 g/g as measured according to the Centrifuge Retention Capacity test set out herein.

2. The absorbent core of claim 1, wherein the one or more nonwoven web(s) have an amount of titratable soluble of less than 20% according to the Titratable Soluble Test Method.

3. The absorbent core of claim 1, wherein the superabsorbent fibers comprises from 0.001 to 1.00 weight-% of surfactant based on the weight of the superabsorbent fibers.

4. The absorbent core of claim 1, wherein the absorbent core has an acquisition time of
less than 120 seconds after the 1st gush,
less than 300 seconds after the 2nd gush, and less than 500 seconds after the 3rd gush, as measured according to the Modified Fluid Acquisition test method.

5. The absorbent core of claim 1, wherein the absorbent core has a length of at least 200 mm as measured along the longitudinal axis of the absorbent core and a maximum width of not more than 170 mm.

6. The absorbent core of claim 1, wherein the absorbent core comprises one or more channels extending completely through the one or more nonwoven webs comprising superabsorbent fibers.

7. The absorbent core of claim 1, wherein the superabsorbent fibers are formed from monomers selected from the group consisting of acrylic acid, methacrylic acid, hydroxyalkyl acrylate, hydroxyalkyl methacrylates, or combinations thereof, e.g. hydroxyethyl methacrylate, tripropyleneglycol mono acrylate, 5 glyceryl monoacrylate, and salts and combinations thereof.

8. The absorbent core of claim 7, wherein the hydroxyalkyl (meth) acrylates are selected from the group consisting of hydroxyethyl methacrylate, tripropyleneglycol mono acrylate, 5 glyceryl monoacrylate, or combinations thereof.

9. The absorbent core of claim 1, wherein the superabsorbent fibers are formed of a combination of at least 3 different monomers.

10. The absorbent core of any of claim 1, wherein the one or more nonwoven webs with superabsorbent fibers are formed of staple fibers.

11. The absorbent core of claim 1, wherein the one or more nonwoven webs with superabsorbent fibers have a porosity of at least 90% as measured according to the porosity test method.

12. The absorbent core of claim 1, wherein the absorbent core comprises channels, wherein the channels extending through the thickness of the absorbent core, or the channels extending through one or more of the nonwoven webs with superabsorbent fibers, and wherein the channels have a width of from 1 mm to 30 mm, a length of at least 20 mm, and a length to width ratio of at least 10 to 1.

13. An absorbent article comprising:
a topsheet;
a backsheet;
an absorbent core positioned between the topsheet and the backsheet, wherein the absorbent core comprising:
one or more nonwoven webs, the one or more nonwoven webs comprising at least 80weight-% of superabsorbent fibers based on the total weight of the nonwoven web, wherein the superabsorbent fibers comprise one or more surfactants; and wherein the absorbent core comprises at least 60 weight-% of the superabsorbent fibers based on the total weight of the absorbent core, wherein the one or more nonwoven webs have an amount of extractables of less than 20 weight-% based on the total weight of the one or more nonwoven webs according to the Extractables Test Method, and wherein the nonwoven webs have a capacity of at least 7 g/g as measured according to the Centrifuge Retention Capacity test set out herein.

14. The absorbent article of claim 13, comprising an acquisition system formed of one or two layers, wherein the acquisition layer is positioned between the absorbent core and the topsheet.

15. The absorbent article of claim 14, wherein the absorbent core and the acquisition system in conjunction have an acquisition time of less than 120 seconds after the 1st gush, less than 300 seconds after the 2nd gush, and less than 500 seconds after the 3rd gush, as measured according to the Modified Fluid Acquisition test method.

16. The absorbent article of claims 13, wherein the absorbent article comprising a longitudinal axis, a total length measured along the longitudinal axis, a front waist edge and a back waist edge; a front waist region, a back waist region, and a crotch region extending between the front and back waist region, wherein each region constitutes ⅓ of the total length, wherein the front waist region extends from the front waist edge onto the crotch region and the back waist region extends from the back waist edge to the crotch region, and wherein the basis weight of the absorbent core is at least 10% higher in the crotch region than in the back waist region.

17. A method of making an absorbent core comprising the steps of a) providing superabsorbent fibers;

b) converting the superabsorbent fibers into a continuous nonwoven web; and c) (i) forming a continuous absorbent core which comprises one or more separate nonwoven webs with superabsorbent fibers and cutting the continuous absorbent core into separate absorbent cores; or (ii) cutting the continuous nonwoven web with superabsorbent fibers into separate nonwoven webs with superabsorbent fibers and forming an absorbent core which comprises one or more of the separate nonwoven webs with superabsorbent fibers;

wherein one or more surfactants are provided on and/or inside the superabsorbent fibers, and/or on the continuous nonwoven web, and/or on the separate sheets of nonwoven web;

and wherein the nonwoven web(s) have an amount of extractables of less than 20 weight-% based on the total weight of the one or more nonwoven webs, according to the Extractable Test Method, and/or wherein the one or more nonwoven webs have an amount of titratable soluble of less than 20% according to the Titratable Soluble Test Method; and wherein the nonwoven webs have a capacity of at least 7 g/g as measured according to the Centrifuge Retention Capacity test; and wherein the absorbent core comprises at least 60 weight-% of the superabsorbent fibers based on the total weight of the absorbent core.

18. The method of claim 17, wherein the surfactant is in a solution which has a water content of less than 10 weight-% based on the total weight of the solution.

19. The method of claim 17, wherein the assembly of one or more nonwoven webs into the absorbent core comprises the provision of at least two of the nonwoven webs in a face to face relationship on top of one another such that the absorbent core comprises more than one layer of the nonwoven web.

* * * * *